(12) United States Patent
Herscher et al.

(10) Patent No.: US 9,277,955 B2
(45) Date of Patent: Mar. 8, 2016

(54) POWER GENERATING AND CONTROL APPARATUS FOR THE TREATMENT OF TISSUE

(75) Inventors: Bret Herscher, Cupertino, CA (US); David Krawzsenek, El Cajon, CA (US); Aaron LaBarge, San Diego, CA (US); Joseluis Espinosa, San Diego, CA (US); Michael Perry, Los Altos, CA (US)

(73) Assignee: Vessix Vascular, Inc., Laguna Hills, CA (US)

( * ) Notice: Subject to any disclaimer, the term of this patent is extended or adjusted under 35 U.S.C. 154(b) by 988 days.

(21) Appl. No.: 13/066,347

(22) Filed: Apr. 11, 2011

(65) Prior Publication Data
US 2012/0095461 A1    Apr. 19, 2012

Related U.S. Application Data

(60) Provisional application No. 61/342,191, filed on Apr. 9, 2010.

(51) Int. Cl.
A61B 18/12 (2006.01)
A61B 18/14 (2006.01)
(Continued)

(52) U.S. Cl.
CPC ......... *A61B 18/1206* (2013.01); *A61B 18/1492* (2013.01); *A61B 17/22012* (2013.01); *A61B 18/245* (2013.01); *A61B 2018/0022* (2013.01); *A61B 2018/00214* (2013.01);
(Continued)

(58) Field of Classification Search
CPC ................ A61B 18/1206; A61B 2018/00642; A61B 2018/00684; A61B 2018/00702; A61B 2018/00779; A61B 2018/00875; A61B 2018/00898
USPC ............................................... 606/27, 34, 41
See application file for complete search history.

(56) References Cited

U.S. PATENT DOCUMENTS

| 164,184 A | 6/1875 | Kiddee |
|---|---|---|
| 1,167,014 A | 1/1914 | O'Brien |

(Continued)

FOREIGN PATENT DOCUMENTS

| CA | 2384866 A1 | 5/2001 |
|---|---|---|
| CN | 101583323 A | 11/2009 |

(Continued)

OTHER PUBLICATIONS

CardioVascular Technologies Inc., "Heated Balloon Device Technology," 11 pages, 2008.

(Continued)

*Primary Examiner* — Michael Peffley
*Assistant Examiner* — Daniel Fowler
(74) *Attorney, Agent, or Firm* — Kacvinsky Daisak Bluni PLLC

(57) ABSTRACT

Apparatus, systems, and methods are provided for the generation and control of energy delivery in a dosage to elicit a therapeutic response in diseased tissue. A balloon catheter can have electrodes attached to a power generator and controller such that the balloon and electrodes contact tissue during energy treatment. Energy selectively may be applied to tissue based on measured impedance to achieve gentle heating. Calibration of the apparatus and identification of attached accessories by computing the circuit impedance prior to energy dosage facilitate regulation of power delivery about a set point. Energy delivery can be controlled to achieve substantially uniform bulk tissue temperature distribution. Energy delivery may beneficially affect nerve activity.

25 Claims, 9 Drawing Sheets

(51) Int. Cl.
  *A61B 17/22* (2006.01)
  *A61B 18/24* (2006.01)
  *A61B 18/00* (2006.01)
  *A61B 18/18* (2006.01)
  *A61N 7/02* (2006.01)

(52) U.S. Cl.
  CPC .............. *A61B 2018/00422* (2013.01); *A61B 2018/00577* (2013.01); *A61B 2018/00642* (2013.01); *A61B 2018/00684* (2013.01); *A61B 2018/00702* (2013.01); *A61B 2018/00875* (2013.01); *A61B 2018/00898* (2013.01); *A61B 2018/1861* (2013.01); *A61N 7/022* (2013.01)

(56) References Cited

U.S. PATENT DOCUMENTS

| | | | |
|---|---|---|---|
| 2,505,358 | A | 4/1950 | Gusberg et al. |
| 2,701,559 | A | 2/1955 | Cooper |
| 3,108,593 | A | 10/1963 | Glassman |
| 3,108,594 | A | 10/1963 | Glassman |
| 3,540,431 | A | 11/1970 | Mobin-Uddin |
| 3,952,747 | A | 4/1976 | Kimmell, Jr. |
| 3,996,938 | A | 12/1976 | Clark, III |
| 4,046,150 | A | 9/1977 | Schwartz et al. |
| 4,290,427 | A | 9/1981 | Chin |
| 4,402,686 | A | 9/1983 | Medel |
| 4,416,277 | A * | 11/1983 | Newton et al. ............. 606/35 |
| 4,483,341 | A | 11/1984 | Witteles et al. |
| 4,574,804 | A | 3/1986 | Kurwa |
| 4,587,975 | A | 5/1986 | Salo et al. |
| 4,649,936 | A | 3/1987 | Ungar et al. |
| 4,682,596 | A | 7/1987 | Bales et al. |
| 4,709,698 | A | 12/1987 | Johnston et al. |
| 4,765,331 | A | 8/1988 | Petruzzi et al. |
| 4,770,653 | A | 9/1988 | Shturman |
| 4,784,132 | A | 11/1988 | Fox et al. |
| 4,784,162 | A | 11/1988 | Ricks et al. |
| 4,785,806 | A | 11/1988 | Deckelbaum |
| 4,788,975 | A | 12/1988 | Shturman et al. |
| 4,790,310 | A | 12/1988 | Ginsburg et al. |
| 4,799,479 | A | 1/1989 | Spears |
| 4,823,791 | A | 4/1989 | D'Amelio et al. |
| 4,830,003 | A | 5/1989 | Wolff et al. |
| 4,849,484 | A | 7/1989 | Heard |
| 4,862,886 | A | 9/1989 | Clarke et al. |
| 4,887,605 | A | 12/1989 | Angelsen et al. |
| 4,907,589 | A * | 3/1990 | Cosman ............. 606/34 |
| 4,920,979 | A | 5/1990 | Bullara |
| 4,938,766 | A | 7/1990 | Jarvik |
| 4,955,377 | A | 9/1990 | Lenno et al. |
| 4,976,711 | A | 12/1990 | Parins et al. |
| 5,034,010 | A | 7/1991 | Kittrell et al. |
| 5,052,402 | A | 10/1991 | Bencini et al. |
| 5,053,033 | A | 10/1991 | Clarke |
| 5,071,424 | A | 12/1991 | Reger |
| 5,074,871 | A | 12/1991 | Groshong |
| 5,098,429 | A | 3/1992 | Sterzer |
| 5,098,431 | A | 3/1992 | Rydell |
| 5,102,402 | A | 4/1992 | Dror et al. |
| RE33,925 | E | 5/1992 | Bales et al. |
| 5,109,859 | A | 5/1992 | Jenkins |
| 5,125,928 | A | 6/1992 | Parins et al. |
| 5,129,396 | A | 7/1992 | Rosen et al. |
| 5,139,496 | A | 8/1992 | Hed |
| 5,143,836 | A | 9/1992 | Hartman et al. |
| 5,156,151 | A | 10/1992 | Imran |
| 5,156,610 | A | 10/1992 | Reger |
| 5,158,564 | A | 10/1992 | Schnepp-Pesch et al. |
| 5,170,802 | A | 12/1992 | Mehra |
| 5,178,620 | A | 1/1993 | Eggers et al. |
| 5,178,625 | A | 1/1993 | Groshong |
| 5,190,540 | A | 3/1993 | Lee |
| 5,191,883 | A | 3/1993 | Lennox et al. |
| 5,211,651 | A | 5/1993 | Reger et al. |
| 5,234,407 | A | 8/1993 | Teirstein et al. |
| 5,242,441 | A | 9/1993 | Avitall |
| 5,251,634 | A | 10/1993 | Weinberg et al. |
| 5,254,098 | A | 10/1993 | Ulrich et al. |
| 5,255,679 | A | 10/1993 | Imran |
| 5,263,493 | A | 11/1993 | Avitall |
| 5,267,954 | A | 12/1993 | Nita et al. |
| 5,277,201 | A | 1/1994 | Stern |
| 5,282,484 | A | 2/1994 | Reger |
| 5,286,254 | A | 2/1994 | Shapland et al. |
| 5,295,484 | A | 3/1994 | Marcus |
| 5,297,564 | A | 3/1994 | Love et al. |
| 5,300,068 | A | 4/1994 | Rosar et al. |
| 5,301,683 | A | 4/1994 | Durkan |
| 5,304,115 | A | 4/1994 | Pflueger et al. |
| 5,304,121 | A | 4/1994 | Sahatjian |
| 5,304,171 | A | 4/1994 | Gregory et al. |
| 5,304,173 | A | 4/1994 | Kittrell et al. |
| 5,306,250 | A | 4/1994 | March et al. |
| 5,312,328 | A | 5/1994 | Nita et al. |
| 5,314,466 | A | 5/1994 | Stern et al. |
| 5,322,064 | A | 6/1994 | Lundquist |
| 5,324,255 | A | 6/1994 | Passafaro et al. |
| 5,326,341 | A | 7/1994 | Lew et al. |
| 5,326,342 | A | 7/1994 | Pflueger et al. |
| 5,330,518 | A | 7/1994 | Neilson et al. |
| 5,333,614 | A | 8/1994 | Feiring |
| 5,342,292 | A | 8/1994 | Nita et al. |
| 5,344,395 | A | 9/1994 | Whalen et al. |
| 5,345,936 | A | 9/1994 | Pomeranz et al. |
| 5,364,392 | A | 11/1994 | Warner et al. |
| 5,365,172 | A | 11/1994 | Hrovat et al. |
| 5,368,557 | A | 11/1994 | Nita et al. |
| 5,368,558 | A | 11/1994 | Nita et al. |
| 5,380,274 | A | 1/1995 | Nita et al. |
| 5,380,319 | A | 1/1995 | Saito et al. |
| 5,382,228 | A | 1/1995 | Nita et al. |
| 5,383,874 | A | 1/1995 | Jackson et al. |
| 5,383,917 | A | 1/1995 | Desai et al. |
| 5,397,301 | A | 3/1995 | Pflueger et al. |
| 5,397,339 | A | 3/1995 | Desai |
| 5,401,272 | A | 3/1995 | Perkins et al. |
| 5,403,311 | A | 4/1995 | Abele et al. |
| 5,405,318 | A | 4/1995 | Nita et al. |
| 5,405,346 | A | 4/1995 | Grundy et al. |
| 5,409,000 | A | 4/1995 | Imran |
| 5,417,672 | A | 5/1995 | Nita et al. |
| 5,419,767 | A | 5/1995 | Eggers et al. |
| 5,427,118 | A | 6/1995 | Nita et al. |
| 5,432,876 | A | 7/1995 | Appeldorn et al. |
| 5,441,498 | A | 8/1995 | Perkins et al. |
| 5,447,509 | A | 9/1995 | Mills et al. |
| 5,451,207 | A | 9/1995 | Yock et al. |
| 5,453,091 | A | 9/1995 | Taylor et al. |
| 5,454,788 | A | 10/1995 | Walker et al. |
| 5,454,809 | A | 10/1995 | Janssen |
| 5,455,029 | A | 10/1995 | Hartman et al. |
| 5,456,682 | A | 10/1995 | Edwards et al. |
| 5,457,042 | A | 10/1995 | Hartman et al. |
| 5,471,982 | A | 12/1995 | Edwards et al. |
| 5,474,530 | A | 12/1995 | Passafaro et al. |
| 5,478,351 | A | 12/1995 | Meade et al. |
| 5,496,311 | A | 3/1996 | Abele et al. |
| 5,496,312 | A | 3/1996 | Klicek |
| 5,498,261 | A | 3/1996 | Strul |
| 5,505,201 | A | 4/1996 | Grill et al. |
| 5,505,730 | A | 4/1996 | Edwards |
| 5,507,744 | A | 4/1996 | Tay et al. |
| 5,522,873 | A | 6/1996 | Jackman et al. |
| 5,531,520 | A | 7/1996 | Grimson et al. |
| 5,540,656 | A | 7/1996 | Pflueger et al. |
| 5,540,679 | A | 7/1996 | Fram et al. |
| 5,540,681 | A | 7/1996 | Strul et al. |
| 5,542,917 | A | 8/1996 | Nita et al. |
| 5,545,161 | A | 8/1996 | Imran |
| 5,562,100 | A | 10/1996 | Kittrell |
| 5,571,122 | A | 11/1996 | Kelly et al. |
| 5,571,151 | A | 11/1996 | Gregory |
| 5,573,531 | A | 11/1996 | Gregory |

(56) References Cited

U.S. PATENT DOCUMENTS

| | | |
|---|---|---|
| 5,573,533 A | 11/1996 | Strul |
| 5,584,831 A | 12/1996 | McKay |
| 5,584,872 A | 12/1996 | Lafontaine et al. |
| 5,588,962 A | 12/1996 | Nicholas et al. |
| 5,599,346 A | 2/1997 | Edwards et al. |
| 5,601,526 A | 2/1997 | Chapelon et al. |
| 5,609,606 A | 3/1997 | O'Boyle |
| 5,626,576 A | 5/1997 | Janssen |
| 5,630,837 A | 5/1997 | Crowley |
| 5,637,090 A | 6/1997 | McGee et al. |
| 5,643,255 A | 7/1997 | Organ |
| 5,643,297 A | 7/1997 | Nordgren et al. |
| 5,647,847 A | 7/1997 | Lafontaine et al. |
| 5,649,923 A | 7/1997 | Gregory et al. |
| 5,651,780 A | 7/1997 | Jackson et al. |
| 5,653,684 A | 8/1997 | Laptewicz et al. |
| 5,662,671 A | 9/1997 | Barbut et al. |
| 5,665,062 A | 9/1997 | Houser |
| 5,665,098 A | 9/1997 | Kelly et al. |
| 5,666,964 A | 9/1997 | Meilus |
| 5,667,490 A | 9/1997 | Keith et al. |
| 5,672,174 A | 9/1997 | Gough et al. |
| 5,676,693 A | 10/1997 | Lafontaine |
| 5,678,296 A | 10/1997 | Fleischhacker et al. |
| 5,681,282 A | 10/1997 | Eggers |
| RE35,656 E | 11/1997 | Feinberg |
| 5,688,266 A | 11/1997 | Edwards et al. |
| 5,693,015 A | 12/1997 | Walker et al. |
| 5,693,029 A | 12/1997 | Leonhardt |
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A | 2/1998 | Stern et al. |
| 5,715,819 A | 2/1998 | Svenson et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton |
| 5,769,847 A | 6/1998 | Panescu et al. |
| 5,769,880 A | 6/1998 | Truckai et al. |
| 5,775,338 A | 7/1998 | Hastings |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy-Chutorian et al. |
| 5,792,105 A | 8/1998 | Lin et al. |
| 5,797,849 A | 8/1998 | Vesely et al. |
| 5,797,903 A | 8/1998 | Swanson et al. |
| 5,800,484 A | 9/1998 | Gough et al. |
| 5,800,494 A | 9/1998 | Campbell et al. |
| 5,807,306 A | 9/1998 | Shapland et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory |
| 5,823,956 A | 10/1998 | Roth et al. |
| 5,827,203 A | 10/1998 | Nita |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,836,874 A | 11/1998 | Swanson et al. |
| 5,836,943 A * | 11/1998 | Miller, III ..................... 606/34 |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A | 2/1999 | Swanson et al. |
| 5,869,127 A | 2/1999 | Zhong |
| 5,871,483 A | 2/1999 | Jackson et al. |
| 5,871,524 A | 2/1999 | Knowlton |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A | 3/1999 | Owens et al. |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell et al. |
| 5,904,697 A | 5/1999 | Gifford et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells, III et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton |
| 5,924,424 A | 7/1999 | Stevens et al. |
| 5,925,038 A | 7/1999 | Panescu et al. |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream et al. |
| 5,957,969 A | 9/1999 | Warner et al. |
| 5,961,513 A | 10/1999 | Swanson et al. |
| 5,964,757 A | 10/1999 | Ponzi et al. |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,971,980 A | 10/1999 | Sherman |
| 5,972,026 A | 10/1999 | Laufer et al. |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy-Chutorian et al. |
| 6,004,269 A | 12/1999 | Crowley et al. |
| 6,004,316 A | 12/1999 | Laufer et al. |
| 6,007,514 A | 12/1999 | Nita |
| 6,010,522 A | 1/2000 | Barbut et al. |
| 6,013,033 A | 1/2000 | Berger et al. |
| 6,014,590 A | 1/2000 | Whayne et al. |
| 6,019,757 A | 2/2000 | Scheldrup |
| 6,022,309 A | 2/2000 | Celliers et al. |
| 6,024,740 A | 2/2000 | Lesh et al. |
| 6,030,611 A | 2/2000 | Gorecki et al. |
| 6,032,675 A | 3/2000 | Rubinsky |

(56) References Cited

U.S. PATENT DOCUMENTS

| | | | |
|---|---|---|---|
| 6,033,357 | A | 3/2000 | Ciezki et al. |
| 6,033,397 | A | 3/2000 | Laufer et al. |
| 6,033,398 | A | 3/2000 | Farley et al. |
| 6,033,399 | A * | 3/2000 | Gines .................. 606/38 |
| 6,036,687 | A | 3/2000 | Laufer et al. |
| 6,036,689 | A | 3/2000 | Tu et al. |
| 6,041,260 | A | 3/2000 | Stern et al. |
| 6,050,994 | A | 4/2000 | Sherman |
| 6,056,744 | A | 5/2000 | Edwards |
| 6,056,746 | A | 5/2000 | Goble et al. |
| 6,063,085 | A | 5/2000 | Tay et al. |
| 6,066,096 | A | 5/2000 | Smith et al. |
| 6,066,139 | A | 5/2000 | Ryan et al. |
| 6,068,638 | A | 5/2000 | Makower |
| 6,068,653 | A | 5/2000 | LaFontaine |
| 6,071,277 | A | 6/2000 | Farley et al. |
| 6,071,278 | A | 6/2000 | Panescu et al. |
| 6,078,839 | A | 6/2000 | Carson |
| 6,079,414 | A | 6/2000 | Roth |
| 6,080,171 | A | 6/2000 | Keith et al. |
| 6,081,749 | A | 6/2000 | Ingle et al. |
| 6,083,159 | A | 7/2000 | Driscoll et al. |
| 6,086,581 | A | 7/2000 | Reynolds et al. |
| 6,091,995 | A | 7/2000 | Ingle et al. |
| 6,093,166 | A | 7/2000 | Knudson et al. |
| 6,096,021 | A | 8/2000 | Helm et al. |
| 6,099,526 | A | 8/2000 | Whayne et al. |
| 6,102,908 | A | 8/2000 | Tu et al. |
| 6,106,477 | A | 8/2000 | Miesel et al. |
| 6,110,187 | A | 8/2000 | Donlon et al. |
| 6,114,311 | A | 9/2000 | Parmacek et al. |
| 6,117,101 | A | 9/2000 | Diederich et al. |
| 6,117,128 | A | 9/2000 | Gregory |
| 6,120,476 | A | 9/2000 | Fung et al. |
| 6,120,516 | A | 9/2000 | Selmon et al. |
| 6,121,775 | A | 9/2000 | Pearlman |
| 6,123,679 | A | 9/2000 | Lafaut et al. |
| 6,123,682 | A | 9/2000 | Knudson et al. |
| 6,123,702 | A | 9/2000 | Swanson et al. |
| 6,123,703 | A | 9/2000 | Tu et al. |
| 6,123,718 | A | 9/2000 | Tu et al. |
| 6,129,725 | A | 10/2000 | Tu et al. |
| 6,135,997 | A | 10/2000 | Laufer et al. |
| 6,139,546 | A * | 10/2000 | Koenig et al. .................. 606/34 |
| 6,142,991 | A | 11/2000 | Schatzberger |
| 6,142,993 | A | 11/2000 | Whayne et al. |
| 6,149,647 | A | 11/2000 | Tu et al. |
| 6,152,899 | A | 11/2000 | Farley et al. |
| 6,152,912 | A | 11/2000 | Jansen et al. |
| 6,156,046 | A | 12/2000 | Passafaro et al. |
| 6,158,250 | A | 12/2000 | Tibbals et al. |
| 6,159,187 | A | 12/2000 | Park et al. |
| 6,159,225 | A | 12/2000 | Makower |
| 6,161,048 | A | 12/2000 | Sluijter et al. |
| 6,162,184 | A | 12/2000 | Swanson et al. |
| 6,165,163 | A | 12/2000 | Chien et al. |
| 6,165,172 | A | 12/2000 | Farley et al. |
| 6,165,187 | A | 12/2000 | Reger |
| 6,168,594 | B1 | 1/2001 | Lafontaine et al. |
| 6,171,321 | B1 | 1/2001 | Gifford, III et al. |
| 6,179,832 | B1 | 1/2001 | Jones et al. |
| 6,179,835 | B1 | 1/2001 | Panescu et al. |
| 6,179,859 | B1 | 1/2001 | Bates et al. |
| 6,183,468 | B1 | 2/2001 | Swanson et al. |
| 6,183,486 | B1 | 2/2001 | Snow et al. |
| 6,190,379 | B1 | 2/2001 | Heuser et al. |
| 6,191,862 | B1 | 2/2001 | Swanson et al. |
| 6,197,021 | B1 | 3/2001 | Panescu et al. |
| 6,200,266 | B1 | 3/2001 | Shokrollahi et al. |
| 6,203,537 | B1 | 3/2001 | Adrian |
| 6,203,561 | B1 | 3/2001 | Ramee et al. |
| 6,210,406 | B1 | 4/2001 | Webster |
| 6,211,247 | B1 | 4/2001 | Goodman |
| 6,216,704 | B1 | 4/2001 | Ingle et al. |
| 6,217,576 | B1 | 4/2001 | Tu et al. |
| 6,219,577 | B1 | 4/2001 | Brown, III et al. |
| 6,228,076 | B1 | 5/2001 | Winston et al. |
| 6,228,109 | B1 | 5/2001 | Tu et al. |
| 6,231,516 | B1 | 5/2001 | Keilman et al. |
| 6,231,587 | B1 | 5/2001 | Makower |
| 6,235,044 | B1 | 5/2001 | Root et al. |
| 6,236,883 | B1 | 5/2001 | Ciaccio et al. |
| 6,237,605 | B1 | 5/2001 | Vaska et al. |
| 6,238,389 | B1 | 5/2001 | Paddock et al. |
| 6,238,392 | B1 | 5/2001 | Long |
| 6,241,666 | B1 | 6/2001 | Pomeranz et al. |
| 6,241,753 | B1 | 6/2001 | Knowlton |
| 6,245,020 | B1 | 6/2001 | Moore et al. |
| 6,245,045 | B1 | 6/2001 | Stratienko |
| 6,248,126 | B1 | 6/2001 | Lesser et al. |
| 6,251,128 | B1 | 6/2001 | Knopp et al. |
| 6,258,087 | B1 | 7/2001 | Edwards et al. |
| 6,273,886 | B1 | 8/2001 | Edwards et al. |
| 6,280,466 | B1 | 8/2001 | Kugler et al. |
| 6,283,935 | B1 | 9/2001 | Laufer et al. |
| 6,283,959 | B1 | 9/2001 | Lalonde et al. |
| 6,284,743 | B1 | 9/2001 | Parmacek et al. |
| 6,287,323 | B1 | 9/2001 | Hammerslag |
| 6,290,696 | B1 | 9/2001 | Lafontaine |
| 6,292,695 | B1 | 9/2001 | Webster, Jr. et al. |
| 6,293,942 | B1 | 9/2001 | Goble et al. |
| 6,293,943 | B1 | 9/2001 | Panescu et al. |
| 6,296,619 | B1 | 10/2001 | Brisken et al. |
| 6,298,256 | B1 | 10/2001 | Meyer |
| 6,299,379 | B1 | 10/2001 | Lewis |
| 6,299,623 | B1 | 10/2001 | Wulfman |
| 6,309,379 | B1 | 10/2001 | Willard et al. |
| 6,309,399 | B1 | 10/2001 | Barbut et al. |
| 6,311,090 | B1 | 10/2001 | Knowlton |
| 6,317,615 | B1 | 11/2001 | KenKnight et al. |
| 6,319,242 | B1 | 11/2001 | Patterson et al. |
| 6,319,251 | B1 | 11/2001 | Tu et al. |
| 6,322,559 | B1 | 11/2001 | Daulton et al. |
| 6,325,797 | B1 | 12/2001 | Stewart et al. |
| 6,325,799 | B1 | 12/2001 | Goble |
| 6,328,699 | B1 | 12/2001 | Eigler et al. |
| 6,346,074 | B1 | 2/2002 | Roth |
| 6,346,104 | B2 | 2/2002 | Daly et al. |
| 6,350,248 | B1 | 2/2002 | Knudson et al. |
| 6,350,276 | B1 | 2/2002 | Knowlton |
| 6,353,751 | B1 | 3/2002 | Swanson et al. |
| 6,355,029 | B1 | 3/2002 | Joye et al. |
| 6,357,447 | B1 | 3/2002 | Swanson et al. |
| 6,361,519 | B1 | 3/2002 | Knudson et al. |
| 6,364,840 | B1 | 4/2002 | Crowley |
| 6,371,965 | B2 | 4/2002 | Gifford, III et al. |
| 6,375,668 | B1 | 4/2002 | Gifford et al. |
| 6,377,854 | B1 | 4/2002 | Knowlton |
| 6,377,855 | B1 | 4/2002 | Knowlton |
| 6,379,352 | B1 | 4/2002 | Reynolds et al. |
| 6,379,373 | B1 | 4/2002 | Sawhney et al. |
| 6,381,497 | B1 | 4/2002 | Knowlton |
| 6,381,498 | B1 | 4/2002 | Knowlton |
| 6,383,151 | B1 | 5/2002 | Diederich et al. |
| 6,387,105 | B1 | 5/2002 | Gifford, III et al. |
| 6,387,380 | B1 | 5/2002 | Knowlton |
| 6,389,311 | B1 | 5/2002 | Whayne et al. |
| 6,389,314 | B2 | 5/2002 | Feiring |
| 6,391,024 | B1 | 5/2002 | Sun et al. |
| 6,394,096 | B1 | 5/2002 | Constantz |
| 6,394,956 | B1 | 5/2002 | Chandrasekaran et al. |
| 6,398,780 | B1 | 6/2002 | Farley et al. |
| 6,398,782 | B1 | 6/2002 | Pecor et al. |
| 6,398,792 | B1 | 6/2002 | O'Connor |
| 6,401,720 | B1 | 6/2002 | Stevens et al. |
| 6,402,719 | B1 | 6/2002 | Ponzi et al. |
| 6,405,090 | B1 | 6/2002 | Knowlton |
| 6,409,723 | B1 | 6/2002 | Edwards |
| 6,413,255 | B1 | 7/2002 | Stern |
| 6,421,559 | B1 | 7/2002 | Pearlman |
| 6,423,057 | B1 | 7/2002 | He et al. |
| 6,425,867 | B1 | 7/2002 | Vaezy et al. |
| 6,425,912 | B1 | 7/2002 | Knowlton |
| 6,427,089 | B1 | 7/2002 | Knowlton |

(56) References Cited

U.S. PATENT DOCUMENTS

| | | | |
|---|---|---|---|
| 6,427,118 | B1 | 7/2002 | Suzuki |
| 6,428,534 | B1 | 8/2002 | Joye et al. |
| 6,428,536 | B2 | 8/2002 | Panescu et al. |
| 6,430,446 | B1 | 8/2002 | Knowlton |
| 6,432,102 | B2 | 8/2002 | Joye et al. |
| 6,436,056 | B1 | 8/2002 | Wang et al. |
| 6,438,424 | B1 | 8/2002 | Knowlton |
| 6,440,125 | B1 | 8/2002 | Rentrop |
| 6,442,413 | B1 | 8/2002 | Silver |
| 6,443,965 | B1 | 9/2002 | Gifford, III et al. |
| 6,445,939 | B1 | 9/2002 | Swanson et al. |
| 6,447,505 | B2 | 9/2002 | McGovern et al. |
| 6,447,509 | B1 | 9/2002 | Bonnet et al. |
| 6,451,034 | B1 | 9/2002 | Gifford, III et al. |
| 6,451,044 | B1 | 9/2002 | Naghavi et al. |
| 6,453,202 | B1 | 9/2002 | Knowlton |
| 6,454,737 | B1 | 9/2002 | Nita et al. |
| 6,454,757 | B1 | 9/2002 | Nita et al. |
| 6,454,775 | B1 | 9/2002 | Demarais et al. |
| 6,458,098 | B1 | 10/2002 | Kanesaka |
| 6,458,121 | B1 * | 10/2002 | Rosenstock et al. ............ 606/34 |
| 6,461,378 | B1 | 10/2002 | Knowlton |
| 6,468,276 | B1 | 10/2002 | McKay |
| 6,468,297 | B1 | 10/2002 | Williams et al. |
| 6,470,216 | B1 | 10/2002 | Knowlton |
| 6,470,219 | B1 | 10/2002 | Edwards et al. |
| 6,471,696 | B1 | 10/2002 | Berube et al. |
| 6,475,213 | B1 | 11/2002 | Whayne et al. |
| 6,475,215 | B1 | 11/2002 | Tanrisever |
| 6,475,238 | B1 | 11/2002 | Fedida et al. |
| 6,477,426 | B1 | 11/2002 | Fenn et al. |
| 6,480,745 | B2 | 11/2002 | Nelson et al. |
| 6,481,704 | B1 | 11/2002 | Koster et al. |
| 6,482,202 | B1 | 11/2002 | Goble et al. |
| 6,484,052 | B1 | 11/2002 | Visuri et al. |
| 6,485,489 | B2 | 11/2002 | Teirstein et al. |
| 6,488,679 | B1 | 12/2002 | Swanson et al. |
| 6,489,307 | B1 | 12/2002 | Phillips et al. |
| 6,491,705 | B2 | 12/2002 | Gifford, III et al. |
| 6,494,891 | B1 | 12/2002 | Cornish et al. |
| 6,497,711 | B1 | 12/2002 | Plaia et al. |
| 6,500,172 | B1 | 12/2002 | Panescu et al. |
| 6,500,174 | B1 | 12/2002 | Maguire et al. |
| 6,508,765 | B2 | 1/2003 | Suorsa et al. |
| 6,508,804 | B2 | 1/2003 | Sarge et al. |
| 6,508,815 | B1 | 1/2003 | Strul et al. |
| 6,511,478 | B1 | 1/2003 | Burnside et al. |
| 6,511,496 | B1 | 1/2003 | Huter et al. |
| 6,511,500 | B1 | 1/2003 | Rahme |
| 6,514,236 | B1 | 2/2003 | Stratienko |
| 6,514,245 | B1 | 2/2003 | Williams et al. |
| 6,514,248 | B1 | 2/2003 | Eggers et al. |
| 6,517,534 | B1 | 2/2003 | McGovern et al. |
| 6,517,572 | B2 | 2/2003 | Kugler et al. |
| 6,522,913 | B2 | 2/2003 | Swanson et al. |
| 6,522,926 | B1 | 2/2003 | Kieval et al. |
| 6,524,274 | B1 | 2/2003 | Rosenthal et al. |
| 6,524,299 | B1 | 2/2003 | Tran et al. |
| 6,527,765 | B2 | 3/2003 | Kelman et al. |
| 6,527,769 | B2 | 3/2003 | Langberg et al. |
| 6,540,761 | B2 | 4/2003 | Houser |
| 6,542,781 | B1 | 4/2003 | Koblish et al. |
| 6,544,780 | B1 | 4/2003 | Wang |
| 6,546,272 | B1 | 4/2003 | MacKinnon et al. |
| 6,547,788 | B1 | 4/2003 | Maguire et al. |
| 6,549,800 | B1 | 4/2003 | Atalar et al. |
| 6,552,796 | B2 | 4/2003 | Magnin et al. |
| 6,554,780 | B1 | 4/2003 | Sampson et al. |
| 6,558,381 | B2 | 5/2003 | Ingle et al. |
| 6,558,382 | B2 | 5/2003 | Jahns et al. |
| 6,564,096 | B2 | 5/2003 | Mest |
| 6,565,582 | B2 | 5/2003 | Gifford, III et al. |
| 6,569,109 | B2 | 5/2003 | Sakurai et al. |
| 6,569,177 | B1 | 5/2003 | Dillard et al. |
| 6,570,659 | B2 | 5/2003 | Schmitt |
| 6,572,551 | B1 | 6/2003 | Smith et al. |
| 6,572,612 | B2 | 6/2003 | Stewart et al. |
| 6,577,902 | B1 | 6/2003 | Laufer et al. |
| 6,579,308 | B1 | 6/2003 | Jansen et al. |
| 6,579,311 | B1 | 6/2003 | Makower |
| 6,582,423 | B1 | 6/2003 | Thapliyal et al. |
| 6,589,238 | B2 | 7/2003 | Edwards et al. |
| 6,592,526 | B1 | 7/2003 | Lenker |
| 6,592,567 | B1 | 7/2003 | Levin et al. |
| 6,595,959 | B1 | 7/2003 | Stratienko |
| 6,600,956 | B2 | 7/2003 | Maschino et al. |
| 6,602,242 | B1 | 8/2003 | Fung et al. |
| 6,602,246 | B1 | 8/2003 | Joye et al. |
| 6,605,061 | B2 | 8/2003 | Vantassel et al. |
| 6,605,084 | B2 | 8/2003 | Acker et al. |
| 6,623,452 | B2 | 9/2003 | Chien et al. |
| 6,623,453 | B1 | 9/2003 | Guibert et al. |
| 6,632,193 | B1 | 10/2003 | Davison et al. |
| 6,632,196 | B1 | 10/2003 | Houser |
| 6,645,223 | B2 | 11/2003 | Boyle et al. |
| 6,648,854 | B1 | 11/2003 | Patterson et al. |
| 6,648,878 | B2 | 11/2003 | Lafontaine |
| 6,648,879 | B2 | 11/2003 | Joye et al. |
| 6,651,672 | B2 | 11/2003 | Roth |
| 6,652,513 | B2 | 11/2003 | Panescu et al. |
| 6,652,515 | B1 | 11/2003 | Maguire et al. |
| 6,656,136 | B1 | 12/2003 | Weng et al. |
| 6,658,279 | B2 | 12/2003 | Swanson et al. |
| 6,659,981 | B2 | 12/2003 | Stewart et al. |
| 6,666,858 | B2 | 12/2003 | Lafontaine |
| 6,666,863 | B2 | 12/2003 | Wentzel et al. |
| 6,669,655 | B1 | 12/2003 | Acker et al. |
| 6,669,692 | B1 | 12/2003 | Nelson et al. |
| 6,673,040 | B1 | 1/2004 | Samson et al. |
| 6,673,064 | B1 | 1/2004 | Rentrop |
| 6,673,066 | B2 | 1/2004 | Werneth |
| 6,673,090 | B2 | 1/2004 | Root et al. |
| 6,673,101 | B1 | 1/2004 | Fitzgerald et al. |
| 6,673,290 | B1 | 1/2004 | Whayne et al. |
| 6,676,678 | B2 | 1/2004 | Gifford, III et al. |
| 6,679,268 | B2 | 1/2004 | Stevens et al. |
| 6,681,773 | B2 | 1/2004 | Murphy et al. |
| 6,682,541 | B1 | 1/2004 | Gifford, III et al. |
| 6,684,098 | B2 | 1/2004 | Oshio et al. |
| 6,685,732 | B2 | 2/2004 | Kramer |
| 6,685,733 | B1 | 2/2004 | Dae et al. |
| 6,689,086 | B1 | 2/2004 | Nita et al. |
| 6,689,148 | B2 | 2/2004 | Sawhney et al. |
| 6,690,181 | B1 | 2/2004 | Dowdeswell et al. |
| 6,692,490 | B1 | 2/2004 | Edwards |
| 6,695,830 | B2 | 2/2004 | Vigil et al. |
| 6,695,857 | B2 | 2/2004 | Gifford, III et al. |
| 6,699,241 | B2 | 3/2004 | Rappaport et al. |
| 6,699,257 | B2 | 3/2004 | Gifford, III et al. |
| 6,702,748 | B1 | 3/2004 | Nita et al. |
| 6,702,811 | B2 | 3/2004 | Stewart et al. |
| 6,706,010 | B1 | 3/2004 | Miki et al. |
| 6,706,011 | B1 | 3/2004 | Murphy-Chutorian et al. |
| 6,706,037 | B2 | 3/2004 | Zvuloni et al. |
| 6,709,431 | B2 | 3/2004 | Lafontaine |
| 6,711,429 | B1 | 3/2004 | Gilboa et al. |
| 6,712,815 | B2 | 3/2004 | Sampson et al. |
| 6,714,822 | B2 | 3/2004 | King et al. |
| 6,716,184 | B2 | 4/2004 | Vaezy et al. |
| 6,720,350 | B2 | 4/2004 | Kunz et al. |
| 6,723,043 | B2 | 4/2004 | Kleeman et al. |
| 6,723,064 | B2 | 4/2004 | Babaev |
| 6,736,811 | B2 | 5/2004 | Panescu et al. |
| 6,743,184 | B2 | 6/2004 | Sampson et al. |
| 6,746,401 | B2 | 6/2004 | Panescu |
| 6,746,464 | B1 | 6/2004 | Makower |
| 6,746,474 | B2 | 6/2004 | Saadat |
| 6,748,953 | B2 | 6/2004 | Sherry et al. |
| 6,749,607 | B2 | 6/2004 | Edwards et al. |
| 6,752,805 | B2 | 6/2004 | Maguire et al. |
| 6,760,616 | B2 | 7/2004 | Hoey et al. |
| 6,763,261 | B2 | 7/2004 | Casscells, III et al. |
| 6,764,501 | B2 | 7/2004 | Ganz |
| 6,769,433 | B2 | 8/2004 | Zikorus et al. |

(56) References Cited

U.S. PATENT DOCUMENTS

| | | |
|---|---|---|
| 6,770,070 B1 | 8/2004 | Balbierz |
| 6,771,996 B2 | 8/2004 | Bowe et al. |
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Döscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,958,075 B2 | 10/2005 | Mon et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,962,587 B2 * | 11/2005 | Johnson et al. ............... 606/41 |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,008,667 B2 | 3/2006 | Chudzik et al. |
| 7,011,508 B2 | 3/2006 | Lum |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |

(56) References Cited

U.S. PATENT DOCUMENTS

| | | |
|---|---|---|
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Christian et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |

(56) References Cited

U.S. PATENT DOCUMENTS

| | | |
|---|---|---|
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |
| 7,744,594 B2 | 6/2010 | Yamazaki et al. |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais |
| 7,854,734 B2 | 12/2010 | Biggs et al. |
| 7,857,756 B2 | 12/2010 | Warren et al. |
| 7,862,565 B2 | 1/2011 | Eder et al. |
| 7,863,897 B2 | 1/2011 | Slocum, Jr. et al. |
| 7,869,854 B2 | 1/2011 | Shachar et al. |
| 7,873,417 B2 | 1/2011 | Demarais et al. |
| 7,887,538 B2 | 2/2011 | Bleich et al. |
| 7,894,905 B2 | 2/2011 | Pless et al. |
| 7,896,873 B2 | 3/2011 | Hiller et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Alejandro et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,048,144 B2 | 11/2011 | Thistle et al. |
| 8,052,636 B2 | 11/2011 | Moll et al. |
| 8,052,700 B2 | 11/2011 | Dunn |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarals et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | LaFontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,287,524 B2 | 10/2012 | Siegel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 | 1/2013 | Stone et al. |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |
| 8,401,667 B2 | 3/2013 | Gustus et al. |
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |

(56) References Cited

U.S. PATENT DOCUMENTS

| | | |
|---|---|---|
| 8,454,594 B2 | 6/2013 | Demarais et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,488,591 B2 | 7/2013 | Miali et al. |
| 2001/0007070 A1 | 7/2001 | Stewart et al. |
| 2001/0039419 A1 | 11/2001 | Francischelli et al. |
| 2001/0051774 A1 | 12/2001 | Littrup et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0062123 A1 | 5/2002 | McClurken et al. |
| 2002/0062146 A1 | 5/2002 | Makower et al. |
| 2002/0065542 A1 | 5/2002 | Lax et al. |
| 2002/0072686 A1 | 6/2002 | Hoey et al. |
| 2002/0077592 A1 | 6/2002 | Barry |
| 2002/0082552 A1 | 6/2002 | Ding et al. |
| 2002/0087151 A1 | 7/2002 | Mody et al. |
| 2002/0087156 A1 | 7/2002 | Maguire et al. |
| 2002/0091381 A1 | 7/2002 | Edwards |
| 2002/0095197 A1 | 7/2002 | Lardo et al. |
| 2002/0107511 A1 | 8/2002 | Collins et al. |
| 2002/0107536 A1 | 8/2002 | Hussein |
| 2002/0143324 A1 | 10/2002 | Edwards |
| 2002/0147480 A1 | 10/2002 | Mamayek |
| 2002/0169444 A1 | 11/2002 | Mest et al. |
| 2002/0198520 A1 | 12/2002 | Coen et al. |
| 2003/0004510 A1 | 1/2003 | Wham et al. |
| 2003/0028114 A1 | 2/2003 | Casscells, III et al. |
| 2003/0050635 A1 | 3/2003 | Truckai et al. |
| 2003/0060857 A1 | 3/2003 | Perrson et al. |
| 2003/0060858 A1 | 3/2003 | Kieval et al. |
| 2003/0065317 A1 | 4/2003 | Rudie et al. |
| 2003/0069619 A1 | 4/2003 | Fenn et al. |
| 2003/0088189 A1 | 5/2003 | Tu et al. |
| 2003/0092995 A1 | 5/2003 | Thompson |
| 2003/0114791 A1 | 6/2003 | Rosenthal et al. |
| 2003/0139689 A1 | 7/2003 | Shturman et al. |
| 2003/0195501 A1 | 10/2003 | Sherman et al. |
| 2003/0199747 A1 | 10/2003 | Michlitsch et al. |
| 2003/0212394 A1 | 11/2003 | Pearson et al. |
| 2003/0220639 A1 | 11/2003 | Chapelon et al. |
| 2003/0229340 A1 | 12/2003 | Sherry et al. |
| 2003/0229384 A1 | 12/2003 | Mon |
| 2004/0000633 A1 | 1/2004 | Arnold et al. |
| 2004/0006359 A1 | 1/2004 | Laguna |
| 2004/0010118 A1 | 1/2004 | Zerhusen et al. |
| 2004/0019348 A1 | 1/2004 | Stevens et al. |
| 2004/0024371 A1 | 2/2004 | Plicchi et al. |
| 2004/0043030 A1 | 3/2004 | Griffiths et al. |
| 2004/0062852 A1 | 4/2004 | Schroeder et al. |
| 2004/0064090 A1 | 4/2004 | Keren et al. |
| 2004/0064093 A1 | 4/2004 | Hektner et al. |
| 2004/0073206 A1 | 4/2004 | Foley et al. |
| 2004/0082946 A1* | 4/2004 | Malis et al. ................ 606/34 |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0111016 A1 | 6/2004 | Casscells, III et al. |
| 2004/0117032 A1 | 6/2004 | Roth |
| 2004/0122421 A1 | 6/2004 | Wood |
| 2004/0147915 A1 | 7/2004 | Hasebe |
| 2004/0162555 A1 | 8/2004 | Farley et al. |
| 2004/0167506 A1 | 8/2004 | Chen |
| 2004/0181165 A1 | 9/2004 | Hoey et al. |
| 2004/0186356 A1 | 9/2004 | O'Malley et al. |
| 2004/0186468 A1 | 9/2004 | Edwards |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0243199 A1 | 12/2004 | Mon et al. |
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0010208 A1 | 1/2005 | Winston et al. |
| 2005/0015125 A1 | 1/2005 | Mioduski et al. |
| 2005/0033136 A1 | 2/2005 | Govari et al. |
| 2005/0080374 A1 | 4/2005 | Esch et al. |
| 2005/0090820 A1 | 4/2005 | Cornelius et al. |
| 2005/0096647 A1 | 5/2005 | Steinke et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0203434 A1 | 9/2005 | Kassab |
| 2005/0203498 A1 | 9/2005 | Mon et al. |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2005/0283195 A1 | 12/2005 | Pastore et al. |
| 2006/0004323 A1 | 1/2006 | Chang et al. |
| 2006/0018949 A1 | 1/2006 | Ammon et al. |
| 2006/0024564 A1 | 2/2006 | Manclaw et al. |
| 2006/0025765 A1 | 2/2006 | Landman et al. |
| 2006/0062786 A1 | 3/2006 | Salcedo et al. |
| 2006/0079882 A1* | 4/2006 | Swoyer et al. ................ 606/41 |
| 2006/0083194 A1 | 4/2006 | Dhrimaj et al. |
| 2006/0085054 A1 | 4/2006 | Zikorus et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0142790 A1 | 6/2006 | Gertner |
| 2006/0147492 A1 | 7/2006 | Hunter et al. |
| 2006/0149166 A1 | 7/2006 | Zvuloni |

(56) References Cited

U.S. PATENT DOCUMENTS

| | | |
|---|---|---|
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0184060 A1 | 8/2006 | Belalcazar et al. |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0224153 A1 | 10/2006 | Fischell et al. |
| 2006/0235286 A1 | 10/2006 | Stone et al. |
| 2006/0239921 A1 | 10/2006 | Mangat et al. |
| 2006/0240070 A1 | 10/2006 | Cromack et al. |
| 2006/0246143 A1 | 11/2006 | Ege |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0269555 A1 | 11/2006 | Salcedo et al. |
| 2006/0271111 A1 | 11/2006 | Demarais et al. |
| 2006/0280858 A1 | 12/2006 | Kokish |
| 2006/0287644 A1 | 12/2006 | Inganas et al. |
| 2006/0293649 A1 | 12/2006 | Lorang et al. |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043409 A1 | 2/2007 | Brian et al. |
| 2007/0049924 A1 | 3/2007 | Rahn |
| 2007/0066972 A1 | 3/2007 | Ormsby et al. |
| 2007/0073151 A1 | 3/2007 | Lee |
| 2007/0078498 A1 | 4/2007 | Rezai et al. |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1 | 6/2007 | Matsukuma et al. |
| 2007/0162109 A1 | 7/2007 | Davila et al. |
| 2007/0173805 A1 | 7/2007 | Weinberg et al. |
| 2007/0173899 A1 | 7/2007 | Levin et al. |
| 2007/0179496 A1 | 8/2007 | Swoyer et al. |
| 2007/0197891 A1 | 8/2007 | Shachar et al. |
| 2007/0203480 A1 | 8/2007 | Mody et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |
| 2008/0021408 A1 | 1/2008 | Jacobsen et al. |
| 2008/0033049 A1 | 2/2008 | Mewshaw |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0064957 A1 | 3/2008 | Spence |
| 2008/0071269 A1 | 3/2008 | Hilario et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281315 A1 | 11/2008 | Gines |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0012514 A1* | 1/2009 | Moonen et al. ............... 606/27 |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0074828 A1 | 3/2009 | Alexis et al. |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Moyer et al. |
| 2009/0216317 A1 | 8/2009 | Cromack et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |

(56) References Cited

U.S. PATENT DOCUMENTS

| | | |
|---|---|---|
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0125239 A1 | 5/2010 | Perry et al. |
| 2010/0125268 A1 | 5/2010 | Gustus et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0204560 A1 | 8/2010 | Salahieh et al. |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249604 A1 | 9/2010 | Hastings et al. |
| 2010/0249702 A1 | 9/2010 | Magana et al. |
| 2010/0249773 A1 | 9/2010 | Clark et al. |
| 2010/0256616 A1 | 10/2010 | Katoh et al. |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |
| 2011/0040324 A1 | 2/2011 | McCarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118598 A1 | 5/2011 | Gertner |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178403 A1 | 7/2011 | Weng et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0307034 A1 | 12/2011 | Hastings et al. |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |

(56) References Cited

U.S. PATENT DOCUMENTS

| | | |
|---|---|---|
| 2013/0035681 A1 | 2/2013 | Subramaniam et al. |
| 2013/0066316 A1 | 3/2013 | Steinke et al. |
| 2013/0085489 A1 | 4/2013 | Fain et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister |
| 2013/0172880 A1 | 7/2013 | Willard |
| 2013/0172881 A1 | 7/2013 | Hill et al. |

FOREIGN PATENT DOCUMENTS

| | | |
|---|---|---|
| CN | 102271607 A | 12/2011 |
| DE | 10038737 A1 | 2/2002 |
| DE | 102005041601 A1 | 4/2007 |
| DE | 102008048616 A1 | 4/2010 |
| EP | 558297 A2 | 9/1993 |
| EP | 647435 A1 | 4/1995 |
| EP | 634910 B1 | 8/1997 |
| EP | 868884 A2 | 10/1998 |
| EP | 1005838 A1 | 6/2000 |
| EP | 1053720 A1 | 11/2000 |
| EP | 1055399 A1 | 11/2000 |
| EP | 1064886 A1 | 1/2001 |
| EP | 1180004 A1 | 2/2002 |
| EP | 1181895 A2 | 2/2002 |
| EP | 1297795 A1 | 6/2002 |
| EP | 1264613 A2 | 12/2002 |
| EP | 1286625 A1 | 3/2003 |
| EP | 1332724 A1 | 8/2003 |
| EP | 1335677 B1 | 8/2003 |
| EP | 866675 B1 | 10/2003 |
| EP | 1433448 A1 | 6/2004 |
| EP | 1442719 A1 | 8/2004 |
| EP | 1547537 A1 | 6/2005 |
| EP | 1634542 A1 | 3/2006 |
| EP | 1698296 A1 | 6/2006 |
| EP | 1709922 A1 | 10/2006 |
| EP | 1874211 A2 | 1/2008 |
| EP | 1906853 A2 | 4/2008 |
| EP | 1946712 A1 | 7/2008 |
| EP | 1961394 A2 | 8/2008 |
| EP | 1715798 B1 | 4/2009 |
| EP | 1620156 B1 | 7/2009 |
| EP | 2076193 A2 | 7/2009 |
| EP | 2091455 A2 | 8/2009 |
| EP | 2092957 A1 | 8/2009 |
| EP | 2197533 A1 | 6/2010 |
| EP | 2208506 A1 | 7/2010 |
| EP | 1579889 B1 | 8/2010 |
| EP | 2241279 A1 | 10/2010 |
| EP | 2092957 B1 | 1/2011 |
| EP | 2329859 A1 | 6/2011 |
| EP | 2349044 A1 | 8/2011 |
| EP | 2027882 B1 | 10/2011 |
| EP | 2378956 A2 | 10/2011 |
| EP | 2037840 B1 | 12/2011 |
| EP | 2204134 B1 | 4/2012 |
| EP | 2320821 B1 | 10/2012 |
| GB | 2313062 A | 11/1997 |
| GB | 2453601 A | 4/2009 |
| GB | 2456301 A | 7/2009 |
| JP | 0779991 A | 3/1995 |
| JP | 1995-213621 A | 8/1995 |
| JP | 1995-313603 A | 12/1995 |
| JP | 2001008944 A | 1/2001 |
| JP | 2003-510126 A | 3/2003 |
| WO | WO 91/03207 A1 | 3/1991 |
| WO | WO 91/17731 A1 | 11/1991 |
| WO | WO 92/22239 A1 | 12/1992 |
| WO | WO 93/20747 A1 | 10/1993 |
| WO | WO 93/20770 A2 | 10/1993 |
| WO | WO 94/18896 A1 | 9/1994 |
| WO | WO 94/28809 A1 | 12/1994 |
| WO | WO 95/01751 A1 | 1/1995 |
| WO | WO 95/31142 A1 | 11/1995 |
| WO | WO 96/34559 A1 | 11/1996 |
| WO | 9639086 A1 | 12/1996 |
| WO | WO 97/03604 A1 | 2/1997 |
| WO | WO 97/17104 A1 | 5/1997 |
| WO | WO 97/20510 A1 | 6/1997 |
| WO | WO 97/32532 A1 | 9/1997 |
| WO | WO 97/40760 A1 | 11/1997 |
| WO | WO 97/45156 A2 | 12/1997 |
| WO | WO 98/18393 A1 | 5/1998 |
| WO | WO 98/29030 A1 | 7/1998 |
| WO | WO 98/34565 A1 | 8/1998 |
| WO | WO 98/35638 A1 | 8/1998 |
| WO | WO 98/40023 A1 | 9/1998 |
| WO | 9858588 A1 | 12/1998 |
| WO | 9900060 A1 | 1/1999 |
| WO | WO 99/00060 A1 | 1/1999 |
| WO | WO 99/16370 A1 | 4/1999 |
| WO | WO 99/21608 A1 | 5/1999 |
| WO | WO 99/34741 A1 | 7/1999 |
| WO | WO 99/44522 A1 | 9/1999 |
| WO | WO 00/01313 A1 | 1/2000 |
| WO | WO 00/10475 A1 | 3/2000 |
| WO | 0047118 A1 | 8/2000 |
| WO | WO 00/51513 A1 | 9/2000 |
| WO | WO 00/59394 A1 | 10/2000 |
| WO | WO 00/62727 A1 | 10/2000 |
| WO | WO 00/64387 A1 | 11/2000 |
| WO | WO 00/69376 A1 | 11/2000 |
| WO | WO 00/72909 A1 | 12/2000 |
| WO | WO 01/22897 A1 | 4/2001 |
| WO | WO 01/37746 A1 | 5/2001 |
| WO | WO 01/87172 A1 | 5/2001 |
| WO | WO 01/74255 A | 10/2001 |
| WO | WO 01/87154 A1 | 11/2001 |
| WO | WO 01/95820 A1 | 12/2001 |
| WO | WO 02/15807 A1 | 2/2002 |
| WO | WO 02/28475 A1 | 4/2002 |
| WO | WO 02/39915 A1 | 5/2002 |
| WO | WO 02/058549 A1 | 8/2002 |
| WO | WO 02/080766 A2 | 10/2002 |
| WO | WO 02/087679 A2 | 11/2002 |
| WO | WO 02/089686 A1 | 11/2002 |
| WO | 03026525 A1 | 4/2003 |
| WO | WO 03/077781 A1 | 9/2003 |
| WO | WO 2004/047659 A2 | 6/2004 |
| WO | WO 2004/049976 A2 | 6/2004 |
| WO | WO 2004/064606 A2 | 8/2004 |
| WO | WO 2004/069300 A2 | 8/2004 |
| WO | WO 2004/076146 A2 | 9/2004 |
| WO | 2004100813 A2 | 11/2004 |
| WO | WO 2004/098694 A1 | 11/2004 |
| WO | 2004110258 A2 | 12/2004 |
| WO | WO 2004/105807 A2 | 12/2004 |

(56) References Cited

FOREIGN PATENT DOCUMENTS

| | | |
|---|---|---|
| WO | WO 2005/007000 A1 | 1/2005 |
| WO | WO 2005/037070 A2 | 4/2005 |
| WO | WO 2005/041748 A2 | 5/2005 |
| WO | WO 2005/074829 A1 | 8/2005 |
| WO | WO 2006/041881 A2 | 4/2006 |
| WO | 2006105121 A2 | 10/2006 |
| WO | WO 2006/105121 A2 | 10/2006 |
| WO | WO 2006/116198 A2 | 11/2006 |
| WO | WO 2007/011634 A1 | 1/2007 |
| WO | WO 2007/014063 A2 | 2/2007 |
| WO | WO 2007/047870 A2 | 4/2007 |
| WO | WO 2007/113865 A1 | 10/2007 |
| WO | WO 2007/135431 A2 | 11/2007 |
| WO | WO 2007/146215 A2 | 12/2007 |
| WO | 2008014465 A2 | 1/2008 |
| WO | WO 2008/003058 A2 | 1/2008 |
| WO | WO 2008/009972 A2 | 1/2008 |
| WO | WO 2008/010150 A2 | 1/2008 |
| WO | WO 2008/036281 A2 | 3/2008 |
| WO | WO 2008/049084 A2 | 4/2008 |
| WO | WO 2008/061152 A2 | 5/2008 |
| WO | WO 2008/102363 A2 | 8/2008 |
| WO | WO 2009/036471 A1 | 3/2009 |
| WO | WO 2009/082635 A1 | 7/2009 |
| WO | WO 2009/088678 A1 | 7/2009 |
| WO | WO 2009/113064 A2 | 9/2009 |
| WO | 2009121017 A1 | 10/2009 |
| WO | WO 2009/121017 A1 | 10/2009 |
| WO | WO 2009/137819 A1 | 11/2009 |
| WO | WO 2010/042653 A1 | 4/2010 |
| WO | WO 2010/048007 A1 | 4/2010 |
| WO | WO 2010/056771 A1 | 5/2010 |
| WO | WO 2010/057043 A1 | 5/2010 |
| WO | 2010067360 A2 | 6/2010 |
| WO | WO 2010/070766 A1 | 6/2010 |
| WO | 2010102310 A2 | 9/2010 |
| WO | WO 2010/099207 A1 | 9/2010 |
| WO | WO 2010/120944 A2 | 10/2010 |
| WO | WO 2010/134503 A1 | 11/2010 |
| WO | 2011005901 A2 | 1/2011 |
| WO | 2011053757 A1 | 5/2011 |
| WO | 2011053772 A1 | 5/2011 |
| WO | WO 2011/055143 A2 | 5/2011 |
| WO | WO 2011/060339 A1 | 5/2011 |
| WO | 2011091069 A1 | 7/2011 |
| WO | 2011130534 A2 | 10/2011 |
| WO | WO 2011/126580 A2 | 10/2011 |
| WO | 2012019156 A1 | 2/2012 |
| WO | 2013049601 A2 | 4/2013 |

OTHER PUBLICATIONS

Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50, No. 2, 6 pages, Feb. 2003.
Lazebnik et al., "Tissue Strain Analytics Virtual Touch Tissue Imaging and Qualification," Siemens Whitepaper, Oct. 2008, 7 pages.
Han et al., "Third-Generation Cryosurgery for Primary and Recurrent Prostate Caner," BJU International, vol. 93, pp. 14-18.
Zhou et al., "Mechanism Research of Ciyoanalgesia," Forefront Publishing Group, 1995.
Florete, "Cryoblative Procedure for Back Pain," Jacksonville Medicine, Oct. 1998, 10 pages.
Stevenson, "Irrigated RF Ablation: Power Titration and Fluid Management for Optimal Safety Efficacy," 2005, 4 pages.
Giliatt et al., "The Cause of Nerve Damage in Acute Compression," Trans Am Neurol Assoc, 1974: 99; 71-4.
Omura et al., "A Mild Acute Compression Induces Neurapraxia in Rat Sciatic Nerve," The International Journal of Neuroscience, vol. 114 (12), pp. 1561-1572.
Baun, "Interaction with Soft Tissue," Principles of General & Vascular Sonography, Chapter 2, pp. 23-24, Before Mar. 2012.
Blue Cross Blue Shield Medicaly Policy, "Surgery Section—MRI-Guided Focused Ultrasound (MRgFUS) for the Treatment of Uterine Fibroids and Other Tumors," 2005, 5 pages.
Gentry et al., "Combines 3D Intracardiac Echo and Ultrasound Ablation," Medical Imaging 2003: Ultrasonic and Signal Processing, vol. 5035, 2003, pp. 166-173.
Lafon et al., "Optmizing the Shape of Ultrasound Transducers for Interstitial Thermal Ablations," MEd Phys. Mar. 2002; 29(3): 290-7 (abstract only).
G. Ter Haar, "Ultrasound Focal Beam Surgery," Ultrasound in Med. & Biol., 1995, vol. 21, No. 9, pp. 1089-1100.
Seip et al., "Transurethral High Intensity Focused Ultrasound: Catheter Based Prototypes and Experimental Results," IEEE Ultrasonics Symposium Proceeding, 2000, 4 pages.
Toytman et al., "Tissue Dissection with Ultrafast Laser Using Extended and Multiple Foci," SPIE Proceeding, Optical Interactions with Tissues and Cells XXI, vol. 7562, 2010, 10 pages.
Zhoue et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.
Brown et al., "Radiofrequency capacitive heaters: the effect of coupling medium resistivity on power absorption along a mouse leg" Phys Med Biol 1993, 38 1-12 (abstract).
Cardiovascular Technologies, Inc., "Heated Balloon Device Technology" [Presentation], 2007-2008, 11 pages total. Retrieved from: <<http://www.cvtechinc.com/pr/presoCVT_Heated_Balloon_Tech.pdf>>.
Carrington, "Future of CVI: It's All About the Plaque." Diagnostic Imaging Special Edition Forum [online] [retrieved on Sep. 3, 2003] Retreived from the Internet:,http://dimag.com/specialedition/cardiacimg.shtml> 5 pages total.
Cimino, "Preventing Plaque Attack", [online] [retrieved on Sep. 3, 2003] Retrieved from the Internet: <http://Masshightech.com/displayarticledetail.ap?art_id=52283&cat_id=10>, 3 pages total.
Dahm et al, "Relation of Degree of Laser Debulking of In-Stent Restenosis as a Predictor of Restenosis Rate", Am J Cardiol, 2002; 90(1): 68-70.
De Korte C L. et al., "Characterization of Placque Components with Intravascular Ultrasound Elastography in Human Femoral and Coronary Arterties In Vitro," Circulation 2000;102:617-623.
Durney C., et al., Radiofrequency Radiation Dosimetry Handbook (with table of contents), Oct. 1986, 4th ed., 7 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/handbook/home.htm.
Fournier-Desseux et al. "Assessment of 1-lead and 2-lead electrode patterns in electrical impedance endotomography", Physiol. Meas. (2005) 26:337-349.
Fujimori et al., "Significant Prevention of In-Stent Restenosis by Evans Blue in Patients with Acute Myocardial Infarction", Abstract #2925, AHA (2002), 1 page total.
Fujita, "Sarpogrelate, An Antagonist of 5-$HT_{2a}$ Receptor Treatment Reduces Restenosis After Coronary Stenting", Abstract #2927, AHA (2002), 1 page total.
Gabriel C, et al., Compilation of the Dielectric Properties of Body Tissues at RF and Microwave Frequencies (with table of contents), Jun. 1996, 17 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Report/Report.html.
Gabriel C, et al., Compilation of the Dielectric Properties of Body Tissues at RF and Microwave Frequencies, Appendi04-10-2009 A, Jun. 1996, 21 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Appendi04-10-2009.A/Appendi04-10-2009.A.html.

(56) References Cited

OTHER PUBLICATIONS

Gabriel C, et al., Compilation of the Dielectric Properties of Body Tissues at RF and Microwave Frequencies, Appendi04-10-2009 C, Jun. 1996, 6 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Appendi04-10-2009.C/Appendi04-10-2009.C.html.
Gregory et al., "Liquid Core Light Guide for Laser Angioplasty", *Journal of Quantum Electronics*, vol. 26, No. 12, (Dec. 1990), pp. 2289-2296.
Intraluminal, Product description [online] [retrieved on Sep. 3, 2003] Retrieved from the Internet: http://www.intraluminal.com/products/inde04-10-2009 .html> 1 page total.
Kaplan et al., "Healing after arterial dilatation with radiofrequency thermal and nonthermal balloon angioplasty systems," J Invest Surg. Jan.-Feb. 1993;6(1):33-52.
Kolata, "New Studies Question Value of Opening Arteries", New York Times [online] [retrieved on Jan. 25, 2005]. Retrieved from the Internet: <http://nytimes.com/2004/03/21/health/21HEAR.html?ei=5070&en=641bc03214e&e04-10-2009 =11067>, 5 pages total.
Konings M K, et al., "Development of an Intravascular Impedance Catheter for Detection of Fatty Lesions in Arteries," IEEE Transactions on Medical Imaging, vol. 51, No. 4, Apr. 2004.
Kurtz et al., "Lamellar Refractive Surgery with Scanned Intrastromal Picosecond and Femtosecond Laser Pulses in Animal Eyes", *J Refract Surg*, vol. 14, (Sep./Oct. 1998), pp. 541-548.
LightLab Imaging Technology, "Advantages of OCT", [online] [retrieved on Sep. 3, 2003]. Retrieved from the Internet: <http:www.lightlabimaging.com/advantage.html> 2 pages total.
LightLab Imaging Technology, "Image Gallery", [online] [retrieved on Sep. 3, 2003]. Retrieved from the Internet: <http:lightlabimaging.com/gallery/cvpstill.html> 4 pages total.
LightLab Imaging Technology, "LightLab Imaging Starts US Cardiology Clinical Investigations", LightLab Company Press Release, [online] [retrieved on Sep. 3, 2003]. Retrieved from the Internet: <http://www.lighlabimaging.com/press/cardtrails.html> 2 pages total.
LightLab Imaging Technology, "LightLab Sees Bright Prospects for Cardiac Application of OCT Technology" *The Graysheet Medical Devices Diagnostics & Instrumentation*, vol. 27, No. 35, (Aug. 27, 2001) [online] [retrieved on Sep. 3, 2003]. Retrieved from the Internet: <http://www.lighlabimaging.com/press/graysheet.html> 1 page total.
LightLab Imaging Technology, "What is OCT?", [online] [retrieved on Sep. 3, 2003]. Retrieved from the Internet: <http:lightlabimaging.com/oct.html.> 2 pages total.
LightLab Imaging Technology, "Why use OCT?", [online] [retrieved on Sep. 3, 2003]. Retrieved from the Internet: <http:lightlabimaging.com/whyoct.html> 2 pages total.
Lima et al., "Efficacy and Safety of Oral Sirolimus to Treat and Prevent In-Stent Restenosis: A Pilot Study Results", Abstract #2929, *AHA* (2002), 1 page total.
Lima et al., "Systemic Immunosuppression Inhibits In-Stent Coronary Intimal Proliferation in Renal Transplant Patients", Abstract #2928, *AHA* (2002), 1 page total.
MIT TechTalk, "Laser Catheter to Aid Coronary Surgery", Jan. 9, 1991 [online] [retrieved on Feb. 7, 2005]. Retrieved from the Internet : <http://web.mit.edu/newsoffice/tt/1991/jan09/24037.html> 4 pages total.
Morice et al., "A Randomized Comparison of a Sirolimus-Eluting Stent With a Standard Stent for Coronary Revascularization", *N. Engl J Med*, vol. 346, No. 23, (Jun. 6, 2002), pp. 1773-1779.
Müller et al., "Effectiveness and Safety of Ultrasonic Atherosclerotic Plaque Ablation: In Vitro Investigation", *CardioVas. Intervent. Radiol.*, (1993) 16: 303-307.

Nair A, et al., "Regularized Autoregressive Analysis of Intravascular Ultrasound Backscatter: Improvement in Spatial Accuracy of Tissue Maps," IEEE Transactions on Ultrasonics, Ferroelectrics, and Frequency Control, vol. 51 No. 4, Apr. 2004.
Popma et al., "Chapter 38—Percutaneous Coronary and Valvular Intervention", Heart Disease: A Textbook of Cardiovascular Medicine, 6th ed., (2001) W.B> Saunders Company, pp. 1364-1405.
Romer et al., "Histopathology of Human Coronary Atherosclerosis by Quantifying Its Chemical Composition with Raman Spectroscopy," Circulation 97:878-885 (1998).
Scheller et al., "Potential Solutions to the Current Problem: Coated Balloon," EuroIntervention, Aug. 4, 2008; Suppl C: C63-66.
Scheller, "Intracoronary Paclitaxel Added to Contrast Media Inhibits In-Stent Restenosis of Porcine Coronary Arteries", Abstract #2227, AHA (2002), 2 pages total.
Shaffer, "Scientific Basis of Laser Energy", *Clin Sports Med* 2002; 21(4):585-598.
Shmatukha A V, et al., "MRI temperature mapping during thermal balloon angioplasty," Phys Med Biol 51, (2006) N163-N171.
Slager et al., "Vaporization of Atherosclerotic Placques by Spark Erosion," J Am Coll Cardiol, vol. 5 (Jun. 1985) pp. 1382-1386.
Stiles et al., "Simulated Charactization of Atherosclerotic Lesions in the Coronary Arteries by Measurement of Bioimpedance," IEEE Transactions on Biomedical Engineering, (Jul. 2003), 5(4):916-921.
Süselbeck et al. "Intravascular electric impedance spectroscopy of atherosclerotic lesions using a new impedance system", Basic Res Cardiol (2005) 100:446-452.
Suselbeck T, et al., "In vivo intravascular electrical impedance spectroscopy using a new catheter with integrated microelectrodes," Basic Res Cardiol 100:28-34 (2005).
Tepe et al., "Local Delivery of Paclitaxel to Inhibit Restenosis During Angioplasty of the Leg," N Engl J Med, Feb. 14, 2008; 358(7): 689-699; retrieved from the Internet: <<http://content.nejm.org/cgi/reprint/358/7/689.pdf>>.
Van Den Berg, "Light Echoes Image the Human Body", *OLE*, Oct. 2001, pp. 35-37.
Volcano Therapeutics, "Product—Functional Measurement", [online] [retrieved on Sep. 3, 2003]. Retrieved from the Internet: <http://www.volcanotherapeutics.com/pages/products/functional_measurement-us.html> 2 pages total.
Examiner's Report of Canadian Patent Application No. 2,539,026, mailed Feb. 6, 2012, 4 pages total.
Office Action issued in Chinese Patent Application No. 200480030163.9, mailed Jan. 16, 2009, 8 pages total.
Office Action issued in Chinese Patent Application No. 200480030163.9, mailed Mar. 28, 2008, 7 pages total.
Office Action issued in Chinese Patent Application No. 200480030163.9, mailed Aug. 31, 2007, 8 pages total.
Office Action issued in Chinese Patent Application No. 200480030163.9, mailed Jul. 31, 2009, 5 pages total.
Supplementary Partial European Search Report of Application No. 04816863.7, mailed May 8, 2009, 7 pages total.
Office Action issued in European Application No. 04816863.7, mailed Jun. 4, 2010, 5 pages total.
Office Action issued in European Application No. 04816863.7, mailed Dec. 5, 2011, 4 pages total.
Office Action issued in European Application No. 04816863.7, mailed Jan. 22, 2010, 6 pages total.
Formal Inquiry issued in Japanese Patent Application No. 2006-526351, mailed Jan. 17, 2012, 5 pages total.
Notice of the Reason for Refusal issued in Japanese Patent Application No. 2006-526351, mailed Apr. 27, 2010, 6 pages total.
Final Decision of Rejection issued in Japanese Patent Application No. 2006-526351, mailed Jan. 18, 2011, 4 pages total.
European Search Report and Search Opinion of EP Patent Application No. 12151957.3, mailed Apr. 16, 2012, 8 pages total.
Office Action issued in Chinese Patent Application No. 200680016424.0, mailed Apr. 13, 2010, 10 pages total.
European Search Report and Search Opinion of EP Patent Application No. 06748830.4, mailed Nov. 16, 2009, 12 pages total.
Partial European Search Report of EP Patent Application No. 11191822.3, mailed Mar. 19, 2012, 7 pages total.

(56) References Cited

OTHER PUBLICATIONS

Office Action issued in Chinese Patent Application No. 20111031923.X, mailed Nov. 17, 2011, 16 pages total.
Office Action issued in Chinese Patent Application No. 20111031923.X, mailed May 22, 2012, 10 pages total.
Examiner's First Report of Australian Patent Application No. 2007310988, mailed May 23, 2012, 4 pages total.
European Search Report and Search Opinion of EP Patent Application No. 07844421.3, mailed Jan. 4, 2010, 15 pages total.
European Search Report and Search Opinion of EP Patent Application No. 12155447.1, mailed May 10, 2012, 6 pages total.
International Search Report and Written Opinion of PCT Application No. PCT/US2009/064027, mailed Jan. 19, 2010, 9 pages total.
European Search Report and Search Opinion of EP Patent Application No. 07844417.1, mailed Nov. 5, 2009.
European Search Report and Search Opinion of EP Patent Application No. 12154120.5, mailed May 8, 2012, 8 pages total.
European Search Report and Search Opinion of EP Patent Application No. 07844424.7, mailed Nov. 11, 2009, 11 pages total.
Partial European Search Report of EP Patent Application No. 12154069.4, mailed May 10, 2012, 5 pages total.
International Search Report and Written Opinion of PCT Application No. PCT/US2009/064465, mailed Jan. 13, 2010, 13 pages total.
International Search Report of PCT Application No. PCT/US09/57728, mailed Nov. 30, 2009, 10 pages total.
International Search Report and Written Opinion of PCT/US2010/034789, mailed Jul. 9, 2010, 13 pages total.
International Search Report and Written Opinion of PCT/US2011/00661, mailed Nov. 18, 2011, 14 pages total.
Brown et al., "Observations on the shrink temperature of collagen and its variations with age and disease," Ann Rheum Dis, Jun. 1, 1958, 17(2):196-208.
Notice of the Reason for Refusal issued in Japanese Patent Application No. 2009-533544, mailed Jun. 19, 2012, 3 pages total.
Summons to Attend Oral Proceedings of EP Patent Application No. 07844424.7, mailed Jul. 5, 2012, 7 pages total.
European Search Report and Search Opinion of EP Patent Application No. 11191822.3, mailed Jun. 13, 2012, 13 pages total.
Office Action issued in European Application No. 07844421.3, mailed Aug. 23, 2012, 5 pages total.
Notice of the Reason for Refusal issued in Japanese Patent Application No. 2009-533546, mailed Jun. 19, 2012, 6 pages total.
Extended European Search Report and Search Opinion of EP Patent Application No. 12154069.4, mailed Sep. 17, 2012, 13 pages total.
Notice of the Reason for Refusal issued in Japanese Patent Application No. 2006-526351, mailed Sep. 18, 2012, 20 pages total.
Office Action issued in Chinese Patent Application No. 201110031923.X, mailed on Sep. 6, 2012, 11 pages total.
Office Action issued in Australian Patent Application No. 2010248955, mailed Sep. 13, 2012, 4 pages total.
Van Den Berg, "Light echoes image the human body," OLE, Oct. 2001, p. 35-37.
"IntraLuminal: Products," IntraLuminal Therapeutics, Inc., 2003, p. 1-9.
"Laser Catheter to Aid Coronary Surgery," TechTalk: MIT, Jan. 9, 1991, p. 1-4.
"Optical Coherence Tomography: LightLab Imaging Starts US Cardiology Clinical Investigations," LightLab Imaging Technology, 2002.
"Optical Coherence Tomography: LightLab Sees Bright Prospects for Cardiac Application of OCT Technology," LightLab Imaging Technology, 2001, vol. 27, No. 35.
"Products—Functional Measurement," VOLCANO Functional Measurement Products US, Mar. 24, 2003, p. 1-2.
Brown et al., "Radiofrequency capacitive heaters: the effect of coupling medium resistivity on power absorption along a mouse leg," Physics in Medicine and Biology, 1993, p. 1-12, vol. 38.
Carrington, "Future of CVI: It's all about plaque: Identification of vulnerable lesions, not 'rusty pipes,' could become cornerstone of preventive cardiology," Diagnostic Imaging, 2001, p. 1-8.

Chen et al., "Percutaneous pulmonary artery denervation completely abolishes experimental pulmonary arterial hypertension in vivo," EuroIntervention, 2013, p. 1-8.
Cimino, "Preventing plaque attack," Mass High Tech, 2001, p. 1-2.
Dahm et al., "Relation of Degree of Laser Debulking of In-Stent Restenosis as a Predictor of Restenosis Rate," The American Journal of Cardiology, 2002, p. 68-70, vol. 90.
De Korte et al., "Characterization of Plaque Components With Intravascular Ultrasound Elastography in Human Femoral and Coronary Arteries In Vitro," Circulation, Aug. 8, 2000, p. 617-623.
Durney et al., "Radiofrequency Radiation Dosimetry Handbook," Oct. 1986, p. 1-2, Fourth Edition.
Durney et al., "Radiofrequency Radiation Dosimetry Handbook: Contents," Oct. 1986, p. 1-5, Fourth Edition.
Fournier-Desseux et al., "Assessment of 1-lead and 2-lead electrode patterns in electrical impedance endotomography," Physiological Measurement, 2005, p. 337-349. Vo. 26, Institute of Physics Publishing.
Fram et al., "Feasibility of Radiofrequency Powered, Thermal Balloon Ablation of Atrioventricular Bypass Tracts Via the Coronary Sinus: In Vivo Canine Studies," PACE, Aug. 1995, p. 1518-1530, vol. 18.
Fram et al., "Low Pressure Radiofrequency Balloon Angioplasty: Evaluation in Porcine Peripheral Arteries," JACC, 1993, p. 1512-1521, vol. 21, No. 6, American College of Cardiology.
Fujimori et al., "Significant Prevention of In-Stent Restenosis by Evans Blue in Patients with Acute Myocardial Infarction," American Heart Association, 2002.
Fujita et al., "Sarpogrelate, An Antagonist of 5-HT(2A) Receptor, Treatment Reduces Restenosis After Coronary Stenting," American Heart Association, 2002.
Gabriel, "Appendix A: Experimental Data," 1999, p. 1-21.
Gabriel, "Appendix C: Modeling the frequency dependence of the dielectric properties to a 4 dispersions spectrum," p. 1-6, 1999 (see above).
Gregory et al., "Liquid Core Light Guide for Laser Angioplasty," The Journal of Quantum Electronics, Dec. 1990, p. 2289-2296, vol. 26, No. 12.
Kaplan et al., "Healing after Arterial Dilatation with Radiofrequency Thermal and Nonthermal Balloon Angioplasty Sytems," Journal of Investigative Surgery, 1993, p. 33-52, vol. 6.
Kolata, "New Studies Question Value of Opening Arteries," The New York Times, Mar. 21, 2004, p. 1-5.
Konings et al., "Development of an Intravascular Impedance Catheter for Detection of Fatty Lesions in Arteries," IEEE Transactions on Medical Imaging, Aug. 1997, p. 439-446, vol. 16, No. 4.
Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.
Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.
Lima et al., "Efficacy and Safety of Oral Sirolimus to Treat and Prevent In-Stent Restenosis: A Pilot Study Results," American Heart Association, 2002, p. 2929.
Lima et al., "Systemic Immunosuppression Inhibits In-Stent Coronary Intimal Proliferation in Renal Transplant Patients," American Heart Association, 2002, p. 2928.
Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.
Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.
Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, vol. 51, No. 4.
Popma et al., "Percutaneous Coronary and Valvular Intervention," p. 1364-1405.

(56) References Cited

OTHER PUBLICATIONS

Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.
Romer et al., "Histopathology of Human Coronary Atherosclerosis by Quantifying Its Chemical Composition With Raman Spectroscopy," Circulation, 1998, p. 878-885, vol. 97.
Schauerte et al., "Catheter Ablation of Cardiac Autonomic Nerves for Prevention of Vagal Atrial Fibrillation," Circulation, 2000, p. 2774-2780, vol. 102.
Scheller et al., "Intracoronary Paclitaxel Added to Contrast Media Inhibits In-Stent Restenosis of Porcine Coronary Arteries," American Heart Association, 2002, p. 2227.
Scheller et al., "Potential solutions to the current problem: coated balloon," EuroIntervention, 2008, p. C63-C66, vol. 4 (Supplement C).
Shaffer, "Scientific basis of laser energy," Clinics in Sports Medicine, 2002, p. 585-598, vol. 21.
Shmatukha et al., "MRI temperature mapping during thermal balloon angioplasty," Physics in Medicine and Biology, 2006, p. N163-N171, vol. 51.
Slager et al., "Vaporization of Atherosclerotic Plaques by Spark Erosion," J Am Coll Cardiol, 1985, p. 21-25.
Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.
Suselbeck et al., "In vivo intravascular electric impedance spectroscopy using a new catheter with integrated microelectrodes," Basic Res Cardiol, 2005, p. 28-34, vol. 100.
Suselbeck et al., "Intravascular electric impedance spectroscopy of atherosclerotic lesions using a new impedance catheter system," Basic Res Cardiol, 2005, p. 446-452, vol. 100.
Tepe et al., "Local Delivery of Paclitaxel to Inhibit Restenosis during Angioplasty of the Leg," The New England Journal of Medicine, 2008, p. 689-699, vol. 358.
"Optical Coherence Tomography: Advantages of OCT," LightLab Imaging Technology, printed Sep. 3, 2003.
"Optical Coherence Tomography: Image Gallery Cardiovascular Procedures," LightLab Imaging Technology, printed Sep. 3, 2003.
"Optical Coherence Tomography: What is OCT?," LightLab Imaging Technology, printed Sep. 3, 2003.
"Optical Coherence Tomography: Why Use OCT?," LightLab Imaging Technology, printed Sep. 3, 2003.
US 8,398,630, 03/2013, Demarais et al. (withdrawn)

* cited by examiner

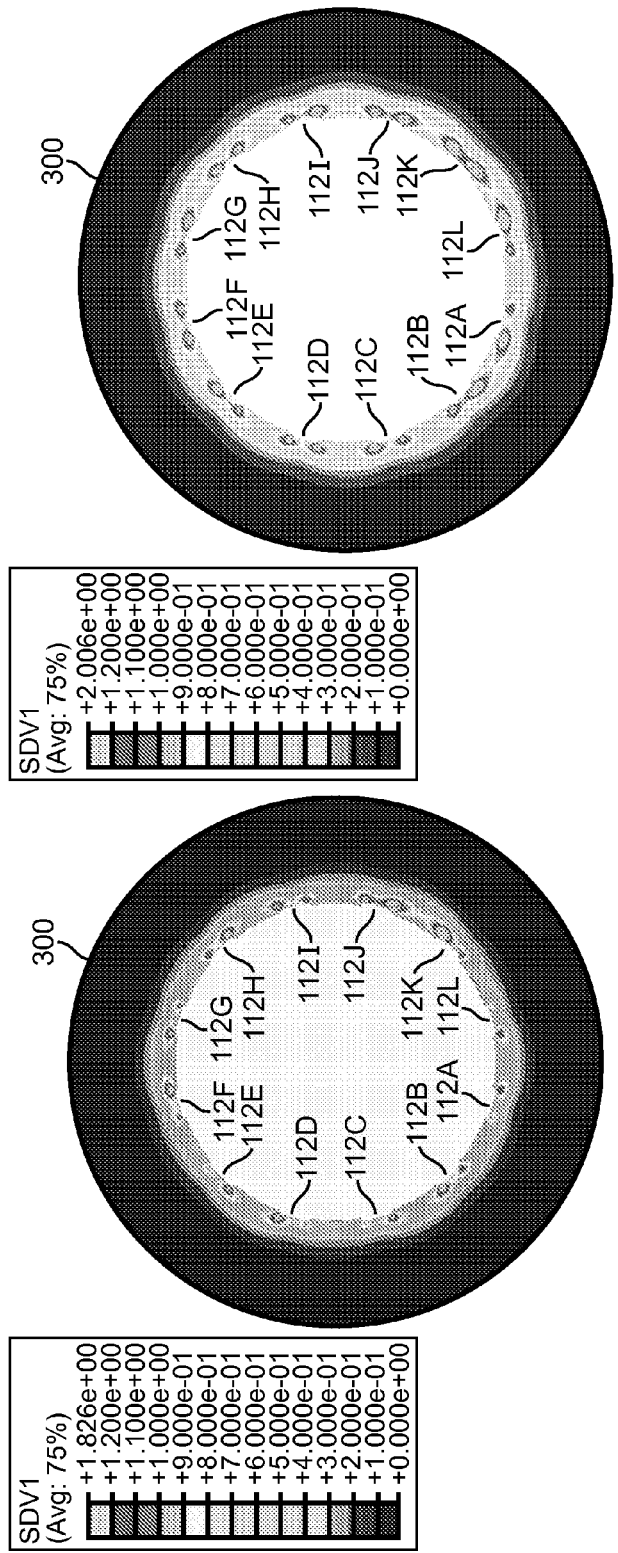

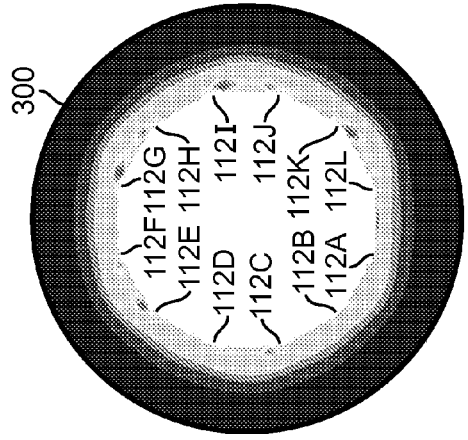
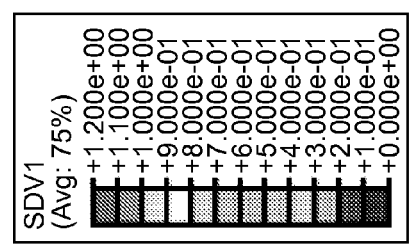
FIG. 15A
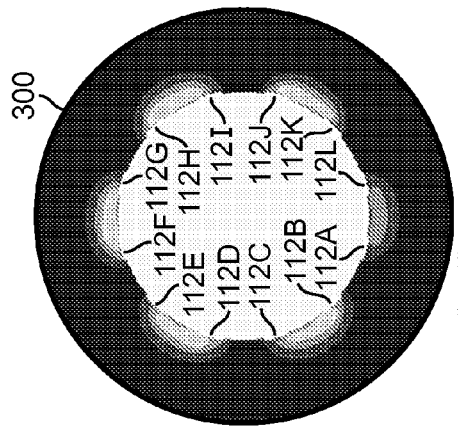
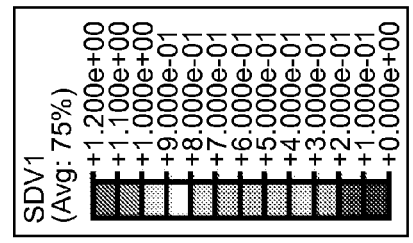
FIG. 15B

POWER GENERATING AND CONTROL APPARATUS FOR THE TREATMENT OF TISSUE

CROSS-REFERENCES TO RELATED APPLICATIONS

The present application claims the benefit under 35 USC 119(e) of U.S. Provisional Application No. 61/342,191 filed Apr. 9, 2010; the full disclosure of which is incorporated herein by reference in its entirety for all purposes.

The subject matter of this application is related to that of U.S. patent application Ser. No. 11/392,231, filed on Mar. 28, 2006, entitled "Tuned RF Energy for Selective Treatment of Atheroma and Other Target Tissues and/or Structures"; U.S. patent application Ser. No. 10/938,138, filed on Sep. 10, 2004, entitled "Selectable Eccentric Remodeling and/or Ablation of Atherosclerotic Material"; U.S. Provisional Application No. 60/852,787, filed on Oct. 18, 2006, entitled "Tuned RF Energy and Electrical Tissue Characterization For Selective Treatment Of Target Tissues"; U.S. Provisional Application No. 60/921,973, filed on Apr. 4, 2007, entitled "Tuned RF Energy and Electrical Tissue Characterization For Selective Treatment Of Target Tissues"; U.S. patent application Ser. No. 11/975,651, filed on Oct. 18, 2007, entitled "Tuned RF Energy and Electrical Tissue Characterization For Selective Treatment Of Target Tissues"; U.S. patent application Ser. No. 12/617,519, filed on Nov. 12, 2009, entitled "Selective Accumulation of Energy With or Without Knowledge of Tissue Topography"; U.S. patent application Ser. No. 11/975,474, filed on Oct. 18, 2007, entitled "Inducing Desirable Temperature Effects on Body Tissue"; U.S. patent application Ser. No. 11/975,383, filed on Oct. 18, 2007, entitled "System for Inducing Desirable Temperature Effects On Body Tissue"; U.S. patent application Ser. No. 12/616,720, filed on Nov. 13, 2009, entitled "Selective Drug Delivery in a Lumen"; U.S. application Ser. No. 12/564,268, filed on Sep. 22, 2009, entitled "Inducing Desirable Temperature Effects on Body Tissue Using Alternate Energy Sources"; and U.S. Provisional Application 61/177,744, filed on May 13, 2009, entitled "Directional Delivery of Energy and Bioactives", the full disclosures of which are incorporated herein by reference.

BACKGROUND OF THE INVENTION

1. Field of the Invention

The present invention is generally related to medical devices, systems, and methods which apply (or otherwise make use of) energy, as well as to other fields in which accurate control over electrical energy is beneficial. In exemplary embodiments, the invention provides an energy generating and control apparatus for the selective delivery of energy dosage during catheter-based treatment for luminal diseases, particularly for atherosclerotic plaque, vulnerable or "hot" plaque, and the like.

2. Discussion of Related Art

Physicians use catheters to gain access to, and repair, interior tissues of the body, particularly within the lumens of the body such as blood vessels. For example, balloon angioplasty and other catheters often are used to open arteries that have been narrowed due to atherosclerotic disease.

Balloon angioplasty is often effective at opening an occluded blood vessel, but the trauma associated with balloon dilation can impose significant injury, so that the benefits of balloon dilation may be limited in time. Stents are commonly used to extend the beneficial opening of the blood vessel.

Stenting, in conjunction with balloon dilation, is often the preferred treatment for atherosclerosis. In stenting, a collapsed metal framework is mounted on a balloon catheter that is introduced into the body. The stent is manipulated into the site of occlusion and expanded in place by the dilation of the underlying balloon. Stenting has gained widespread acceptance, and produces generally acceptable results in many cases. Along with treatment of blood vessels, particularly the coronary arteries, stents can also be used in treating many other tubular obstructions within the body, such as for treatment of reproductive, gastrointestinal, and pulmonary obstructions.

Restenosis or a subsequent narrowing of the body lumen after stenting has occurred in a significant number of cases. More recently, drug coated stents (such as Johnson and Johnson's Cypher™ stent, the associated drug comprising Sirolimus™) have demonstrated a markedly reduced restenosis rate, and others are developing and commercializing alternative drug eluting stents. In addition, work has also been initiated with systemic drug delivery (intravenous or oral) that may also improve the procedural angioplasty success rates.

While drug-eluting stents appear to offer significant promise for treatment of atherosclerosis in many patients, there remain many cases where stents either cannot be used or present significant disadvantages. Generally, stenting leaves an implant in the body. Such implants can present risks, including mechanical fatigue, corrosion, and the like, particularly when removal of the implant is difficult and involves invasive surgery. Stenting may have additional disadvantages for treating diffuse artery disease, for treating bifurcations, for treating areas of the body susceptible to crush, and for treating arteries subject to torsion, elongation, and shortening.

A variety of modified restenosis treatments or restenosis-inhibiting occlusion treatment modalities have also been proposed, including intravascular radiation, cryogenic treatments, ultrasound energy, and the like, often in combination with balloon angioplasty and/or stenting. While these and different approaches show varying degrees of promise for decreasing the subsequent degradation in blood flow following angioplasty and stenting, the trauma initially imposed on the tissues by angioplasty remains problematic.

More recently, still further disadvantages of dilation have come to light. These include the existence of vulnerable plaque, which can rupture and release materials that may cause myocardial infarction or heart attack.

A number of alternatives to stenting and balloon angioplasty so as to open stenosed arteries have also been proposed. For example, a wide variety of atherectomy devices and techniques have been disclosed and attempted. Despite the disadvantages and limitations of angioplasty and stenting, atherectomy has not gained the widespread use and success rates of dilation-based approaches.

Additionally, methods in the art of debulking diseased tissue to reduce or eliminate lesions, such as atherectomy and ablation, generally provide few if any means for protecting healthy tissue from being damaged through the course of treating diseased tissue.

In light of the above, it would be advantageous to provide new devices, systems, and methods for remodeling of the lumens of the body, and particularly tissue of the blood vessels. It would further be desirable to avoid significant cost or complexity while providing structures which could remodel body lumens without having to resort to the trauma of extreme dilation, damage to neighboring healthy tissue, and to allow the opening of blood vessels and other body lumens which are not suitable for stenting.

BRIEF SUMMARY OF THE INVENTION

The present invention relates to the treatment of tissue through the delivery of energy in a controlled dosage. Tissue may be targeted by applying energy, making tissue characterization analysis, and further selectively energizing a plurality of energy delivery surfaces through the use of an energy source with a controller.

In exemplary embodiments, the apparatus for power delivery may comprise a power generating circuit further comprising: a power generating source, an amplifier block, a power output set point controller, voltage and current feedback at the point of power delivery used to measure impedance at the power delivery target, a peak effective power sensor block receiving the voltage and current feedback, and a Proportional, Integral, Derivative (PID) controller receiving a signals from the power output set point controller and the peak effective power sensor block, whereby the PID controller modulates total input voltage to the power amplifier block such that the output of power from the circuit is maintained within a range about the power output set point in response to measured impedance at the power delivery target.

In some exemplary embodiments output power is Radio Frequency (RF) power while in alternate exemplary embodiments power may be in the form of ultrasound, microwave, laser, or other suitable forms of energy.

In some exemplary embodiments the apparatus for delivery may be further comprised of a catheter, wherein the catheter may be further comprised to have a plurality of energy delivery surfaces, most preferably a plurality of energy delivery surfaces mounted to an inflatable balloon.

In some exemplary embodiments there is provided a method for preferably calibrating the apparatus comprised of using a variety of loads to calculate power circuit impedance with vector network analysis such that the measure of real-time change in circuit load impedance during power generation may represent the real-time change in impedance at the power delivery target of the apparatus.

In some exemplary embodiments there is provided a method comprising identifying an accessory attached to the apparatus by repeating calibration to ascertain the type of attached accessory based on its impedance characteristics.

In some exemplary embodiments there is provided a method of applying energy in a controlled manner to achieve a substantially uniform bulk temperature distribution in target tissue.

In some exemplary embodiments there is provided a method for applying energy to nerve tissue to alter the activity of the nerve for the purpose of achieving a beneficial biological response.

Preferred embodiments of the present invention may be used in procedures for achieving therapeutic biologic effects in tissue. Most preferably, the present invention may be used at any point and time before, during, and/or after an angioplasty procedure.

In another aspect, the invention provides a power generating apparatus for treatment of a target tissue. The power generating apparatus comprises a frequency synthesizer generating a frequency signal. A power amplifier operatively couples the frequency synthesizer to a power output. The output is coupleable to the target tissue, and a power sensor is configured to receive voltage and current feedback from the target tissue, and to output measured impedance at the target tissue. A controller couples the power sensor to the power amplifier. The controller has an input for receiving a power set point and transmits, in response to the power set point and the measured impedance at the target tissue, a modulating signal to the power amplifier such that power output from the power amplifier to the target tissue per the frequency signal is maintained within a desired range about the power set point.

Optionally, the frequency synthesizer comprises a digital frequency synthesizer such as a Direct Digital Synthesizer (DDS), and a digital-to-analog converter couples the frequency synthesizer to the power amplifier. The energy output from the apparatus to the target tissue typically comprises RF energy, but may alternatively comprise microwave energy or the like. In many embodiments, the power generating apparatus is included in a system, with the system also including an elongate catheter. The catheter may have an elongate flexible catheter body with a distal end configured for advancing into a blood vessel. A connector can be coupled to a proximal end of the body, with the connector being configured to couple to the output so that, in use, the catheter couples the output to the target tissue adjacent the distal end. The impedance of the target tissue as measured by the power generating apparatus of the system is often independent of an impedance of the power generating apparatus, the catheter body, and/or the like.

In another aspect, the invention provides a calibration module for calibrating an RF system in preparation for treatment of a target tissue. The RF system comprises a power generating apparatus including an impedance measurement circuit. The module comprises a first input for receiving a first impedance from the impedance measurement circuit of the power generating apparatus. The first impedance corresponding to a low circuit load on the power generating apparatus prior to coupling of the power generating apparatus to the target tissue. A second input similarly receives a second impedance from the impedance measurement circuit but corresponding to a high circuit load on the power generating apparatus (again prior to coupling of the power generating apparatus to the target tissue). A third input receives a similar third impedance from the impedance measurement circuit between the high load and the low load. A processor is configured to calculate system impedance using the measured impedances so as to facilitate, in response to a measure of real-time changes in overall circuit load impedance during power application to the target tissue, changes in impedance at the target tissue. The overall circuit load impedance comprising impedance of the power generating apparatus and the impedance at target tissue.

Typically, the RF system further comprises a catheter or other coupling device for coupling the power generating apparatus to the target tissue. More generally, the overall circuit of the systems described herein may, during use, include a power generating circuit, a power output target circuit, and a coupling circuit, with each of these portions of the overall system circuit contributing respective impedance portions to the overall impedance of the system. To help more accurately characterize the impedance contributions of these portions of the overall circuit, and to more accurately measure impedance at the target tissue (or other power output target), the processor can be configured to calculate another system impedance of the power generating apparatus and the catheter after coupling of the catheter to the power generating apparatus and before coupling of the catheter to the target tissue.

BRIEF DESCRIPTION OF THE DRAWINGS

FIGS. 14A & B schematically illustrate a substantially uniform bulk temperature distribution in luminal tissue using empirically derived energy dosage and impedance control for an embodiment of the apparatus shown in FIG. 1.

FIGS. 15A & B schematically illustrate a substantially uniform bulk temperature distribution in luminal tissue using energy dosage derived using accumulated damage theory for an embodiment of the apparatus shown in FIG. 1.

DETAILED DESCRIPTION OF THE INVENTION

Embodiments of the present invention relate to a power generating and control apparatus, often for the treatment of targeted tissue in order to achieve a therapeutic effect. Preferably, the target tissue is luminal tissue, which may further comprise diseased tissue such as that found in arterial disease.

While the disclosure focuses on the use of the technology in the vasculature, the technology would also be useful for other luminal obstructions. Other anatomical structures in which the present invention may be used are the esophagus, the oral cavity, the nasopharyngeal cavity, the auditory tube and tympanic cavity, the sinus of the brain, the arterial system, the venous system, the heart, the larynx, the trachea, the bronchus, the stomach, the duodenum, the ileum, the colon, the rectum, the bladder, the ureter, the ejaculatory duct, the vas deferens, the urethra, the uterine cavity, the vaginal canal, and the cervical canal.

Devices for heating tissue using RF, ultrasound, microwave and laser energies have been disclosed in U.S. patent application Ser. No. 11/975,474, filed on Oct. 18, 2007, entitled "Inducing Desirable Temperature Effects on Body Tissue", U.S. patent application Ser. No. 11/975,383, filed on Oct. 18, 2007, entitled "System for Inducing Desirable Temperature Effects On Body Tissue", U.S. patent application Ser. No. 11/122,263, filed on May 3, 2005, entitled "Imaging and Eccentric Atherosclerotic Material Laser Remodeling and/or Ablation Catheter" and U.S. application Ser. No. 12/564,268, filed on Sep. 22, 2009, entitled "Inducing Desirable Temperature Effects on Body Tissue Using Alternate Energy Sources", the full disclosures of which are incorporated herein by reference, may be combined with the present invention.

Power Generation and Control

In many embodiments of the present invention, the power generating and control apparatus may include internal circuitry 400, control software, a user interface 102, and power generation and control enclosure 101 housing the circuitry 400 and user interface 102.

Figure 1:
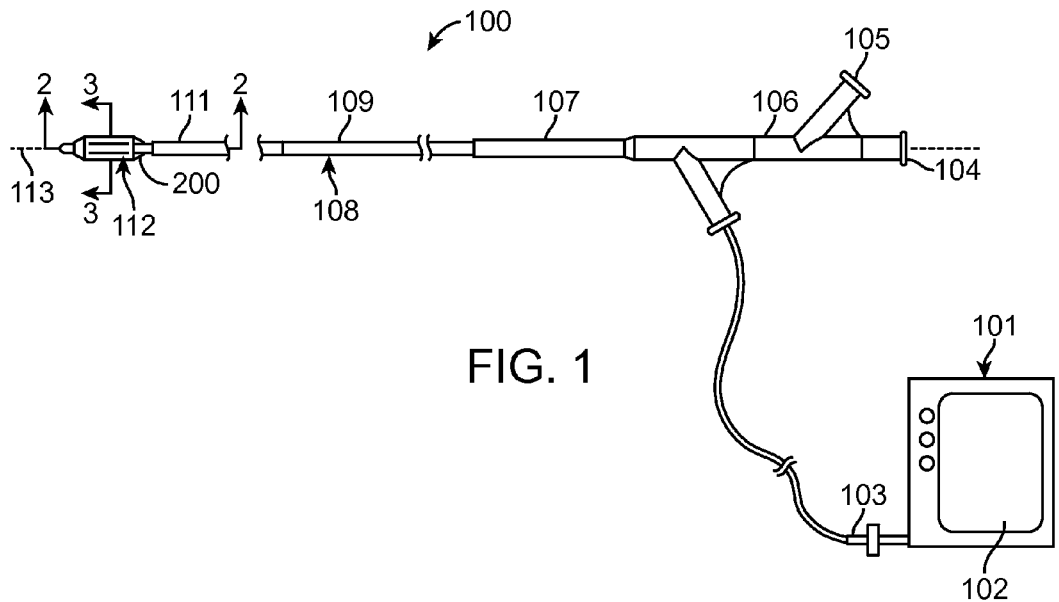
FIG. 1 schematically illustrates one embodiment of a power generation and control apparatus for use with a balloon catheter having electrodes in a power system.
Figure 4:
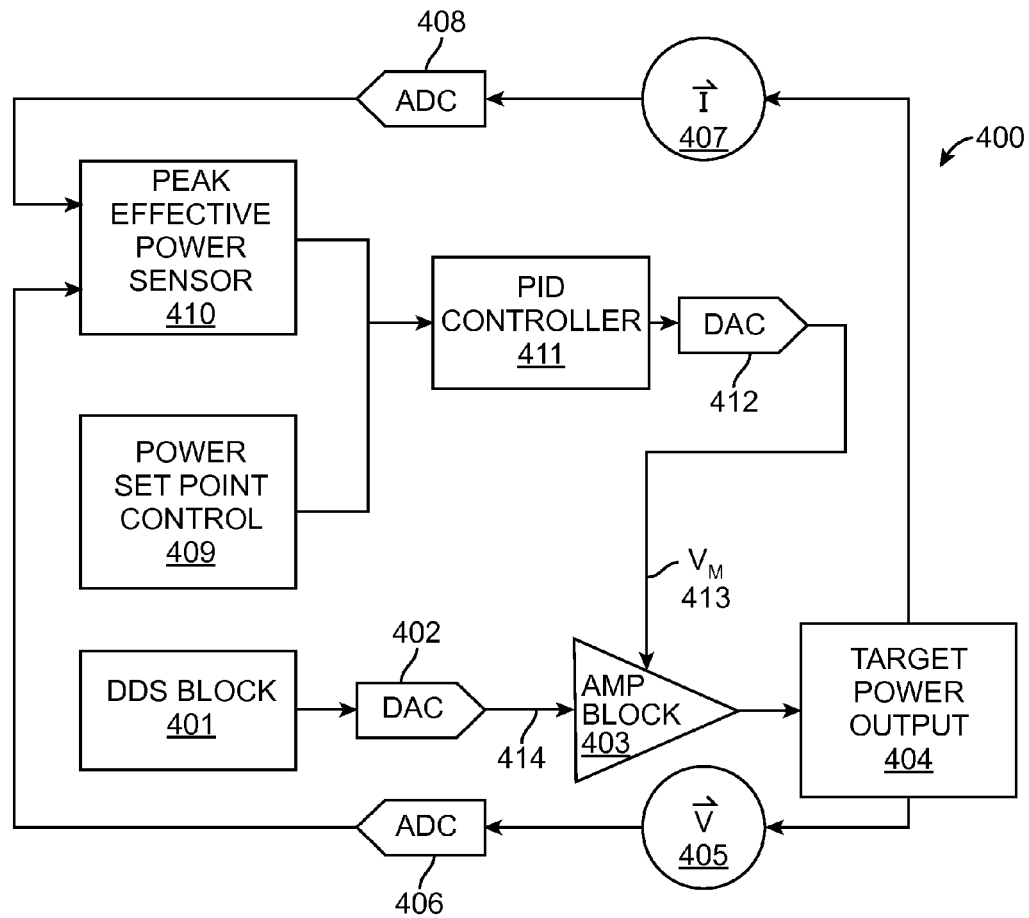
FIG. 4 schematically illustrates one embodiment of a power generation and control circuit.

Referring to FIGS. 1 and 4, the internal circuitry 400, housed within the enclosure 101, may include a direct digital synthesizer (DDS) block 401 whose digital code output may be preferably passed through digital-to-analog converter (DAC) 402. DAC 402 converts the digital code signal from DDS block 401 to an analog voltage signal 414. Voltage signal 414 and an analog modulating voltage signal 413 preferably pass through amplifier block 403, resulting in target power output 404. Measurements of voltage and current load at the target power output 404 may be measured by voltage sensor 405 and current sensor 407, preferably the signals from which may be passed through analog-to-digital converters (ADC) 406 and 408 respectively. The digital voltage signal from ADC 406 and the digital current signal from ADC 408 are preferably received by peak effective power sensor 410, where the effective power output of the power generation and control apparatus at the power delivery target 404 may be measured in real-time. Power set point control 409 is based on software-programmed operating parameters.

Figure 5:
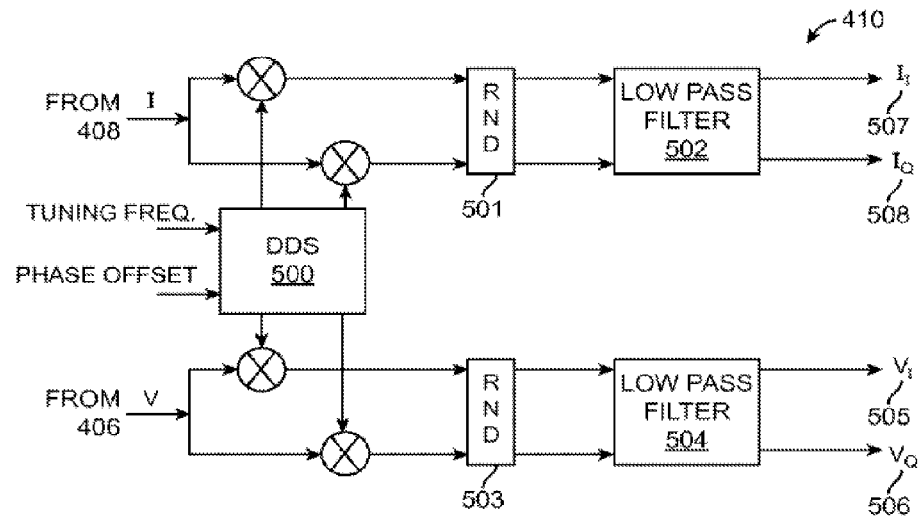
FIG. 5 schematically illustrates one embodiment of a DDS down conversion section of a peak effective power sensor block shown in FIG. 4.
Figure 6:
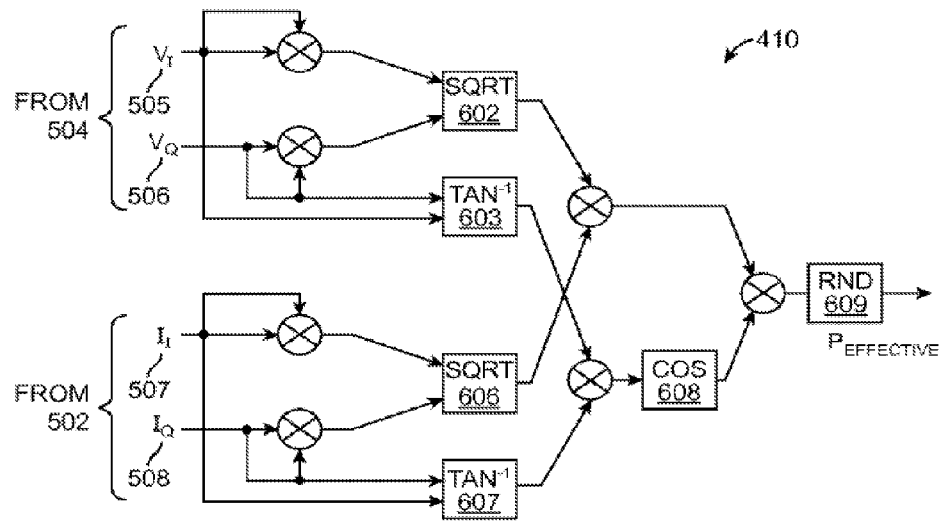
FIG. 6 schematically illustrates one embodiment of the DC baseband processing section of a peak effective power sensor block shown in FIG. 4.

In a preferred embodiment shown in FIGS. 5 and 6, the peak effective power sensor block 410 may comprise a DDS 500 used to mix voltage sense signal V (from 406) and current sense signal I (from 408) down to DC baseband signals, preferably generating a voltage output with low-pass filter 502 after passing sense signal V through rounding gate 501, and a current output with low-pass filter 504 after passing sense signal I through rounding gate 503. The voltage and current output from target power output 404 include in-phase current 507, in-phase voltage 505, and quadrature current 508, quadrature voltage 506 components. It is preferable for signals within the circuit 410 to comprise in-phase and quadrature components because blocks within the circuit 410 may then recognize the instantaneous amplitude, frequency, and phase shift between the components of a signal and between the several signals passing through the blocks of circuit 410. The digital output signals from low-pass filter 502 and low-pass filter 504 of peak effective power sensor 410 may then be transmitted to the power calculation circuits shown in FIG. 6.

Now referring to FIG. 6, voltage amplitude may be calculated by summing the squares of the in-phase voltage signal 505 and the quadrature voltage signal 506, and passing the sum through square root circuit 602. Current amplitude may be calculated by summing the squares of the in-phase current signal 507 and the quadrature current signal 508, and passing the sum through square root circuit 606. Uncorrected power may preferably be calculated by multiplying voltage amplitude and current amplitude.

The phase of the voltage signal may preferably be calculated by passing the quadrature component 506 of the voltage signal and the in-phase component 505 of the voltage signal through inverse tangent gate 603. Similarly, the phase of the current signal may preferably be calculated by passing the quadrature component 508 of the current signal and the in-phase component 507 of the current signal through inverse tangent gate 607. Cosine gate 608 preferably receives the difference output from inverse tangent gates 603 and 607 such that a power factor correction may be calculated. The peak effective power may be calculated by multiplying the uncorrected power by the output of the cosine gate 608 and rounding the result with rounding gate 609.

Although FIGS. 5 and 6 represent a most preferred embodiment, peak effective power may be calculated using other means, such as multiplying the instantaneous RF voltage and RF current waveforms together and integrating the resulting signal to obtain an average value; the means for calculating peak effective power being selected from any available means suitable for the type of power used and suitable for the components comprising the circuitry of the apparatus disclosed and described herein.

Figure 9A:
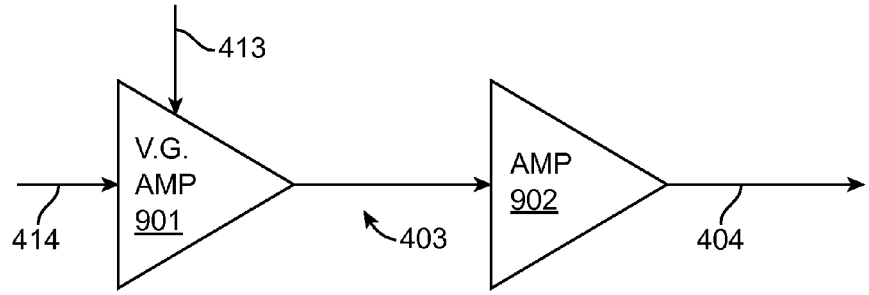
FIG. 9A schematically illustrates one embodiment of the amplifier block shown in FIG. 4.
Figure 9B:
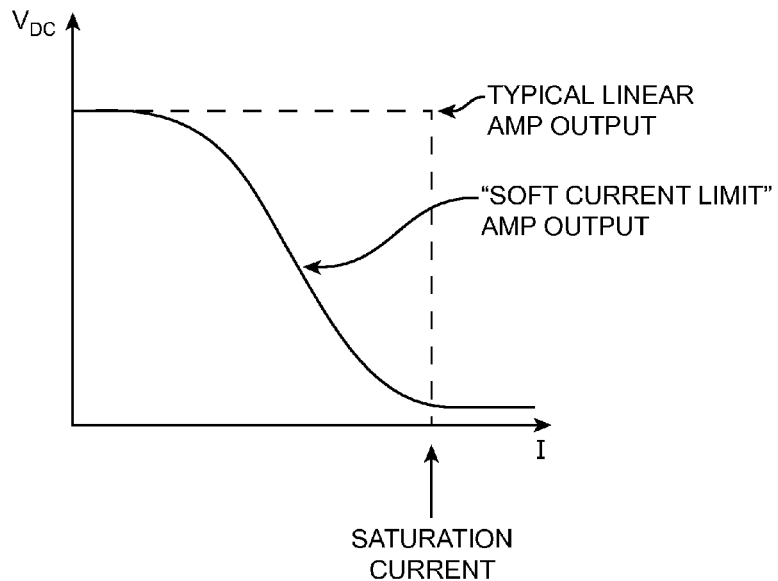
FIG. 9B illustrates the "soft current limit" relationship for the amplifier block shown in FIG. 4.
Figure 10:
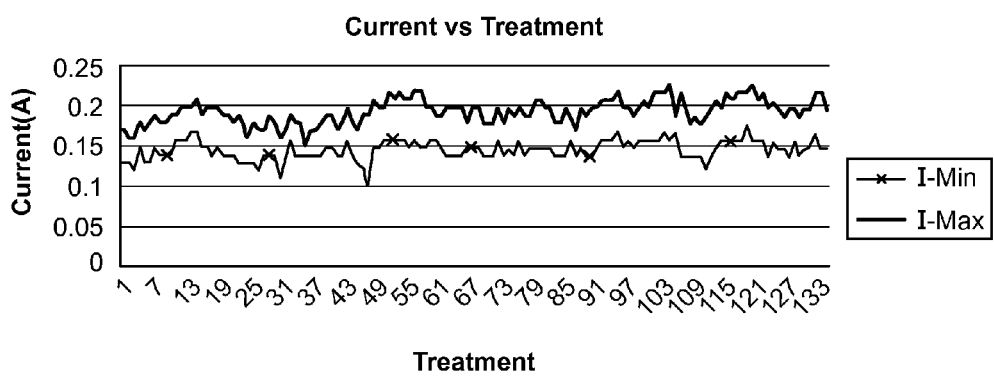
FIG. 10 is an exemplary plot of maximum and minimum measured current in a tissue treatment embodiment of the apparatus shown in FIG. 1.
Figure 11:
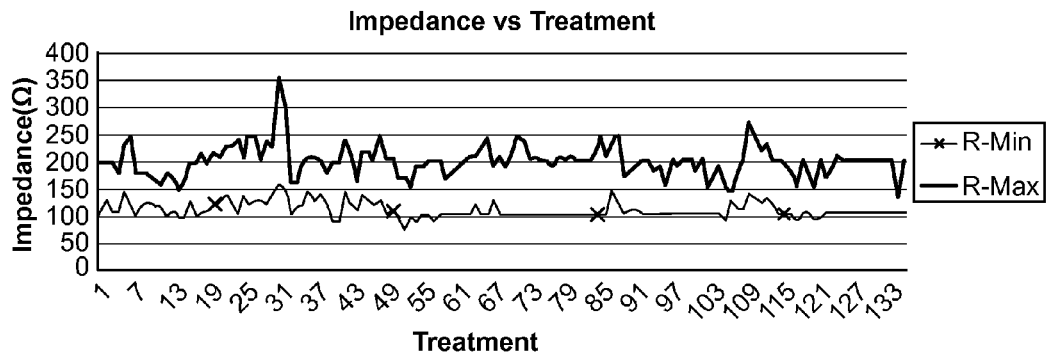
FIG. 11 is an exemplary plot of maximum and minimum measured impedance in a issue treatment embodiment of the apparatus shown in FIG. 1.
Figure 12:
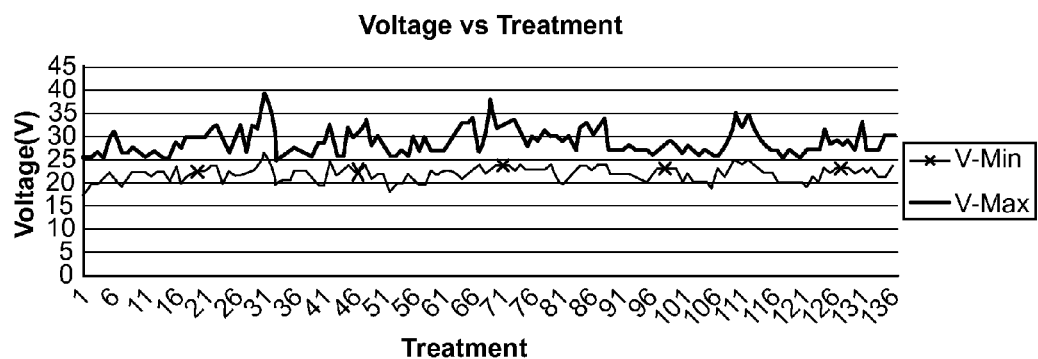
FIG. 12 is an exemplary plot of maximum and minimum measured voltage in a tissue treatment embodiment of the apparatus shown in FIG. 1.

Now referring to FIGS. 9A and 9B, amplifier block 403 may include variable gain amplifier 901, receiving voltage input 414 from DDS block 400 and modulating voltage signal 413 from PID controller 411, and power amplifier 902. Power amplifier 902 has a "soft current limit" as shown in FIG. 9B, whereby the available output voltage decreases in a tailored manner as the required output current is increased. The advantage of power amplifier 902 having a soft current limit is that the maximum output power delivered can be inherently limited by the characteristic of the current limit circuit, wherein the current limit circuit may provide a substantially constant maximum available output power across a broad range of load impedances, most preferably exceeding about a decade of load impedance. An additional advantage of the soft current limit scheme is that, when implemented using switched mode power supply technology, extremely high power amplifier efficiencies can be achieved across a broad range of load impedances, preferably exceeding about a decade of load impedance.

Control of target power output 404 may be preferably achieved through power set point control 409, and peak effective power sensor block 410 passing signals to PID controller 411 that may ultimately produce modulating voltage signal 413 passing into amplifier block 403. Power output set point control 409 may provide a software control signal based on programmed operating parameters, which in many embodiments may be set to promote remodeling of diseased tissue in a manner that avoids damage to surrounding healthy tissue. By taking real-time load measurements in-phase and in quadrature at power output 404, circuit 400 is thereby able to characterize and respond to load variations by modulating output such that output may vary within a relatively small range from set point. Power output variation about the set point may be about ±2%, however, preferred embodiments may regulate output variation in other ranges, such as, about ±5%, about ±10%, about ±15%, and about ±20% or greater.

Figure 7:
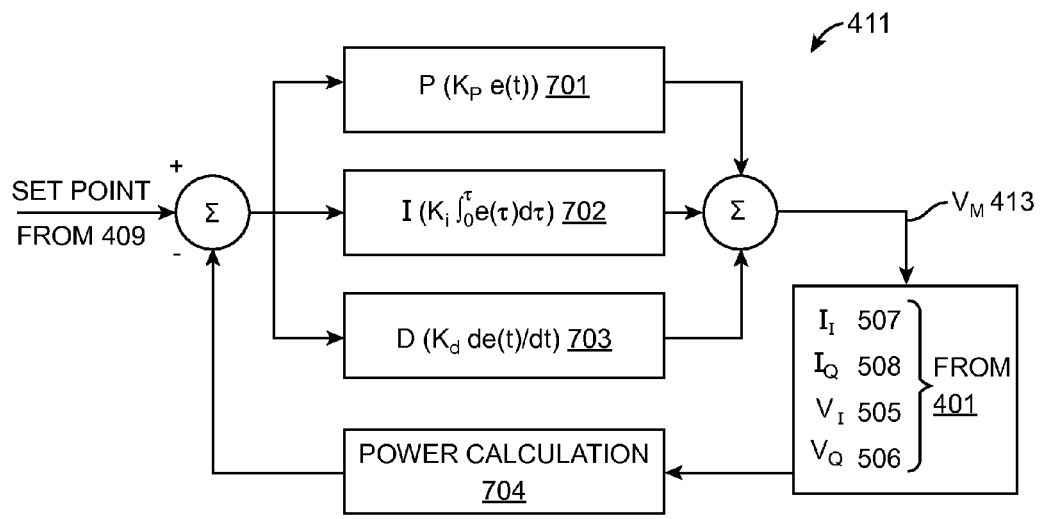
FIG. 7 schematically illustrates one embodiment of a PID control block shown in FIG. 4.

Now referring to FIGS. 4 and 7, PID controller 411 preferably receives output signals from power output set point 409 and peak effective power output block 410. PID controller 411 may comprise hardware and or software modules which perform proportional 701 ("P"), integral 702 ("I"), and derivative 703 ("D") calculations $K_p e(t)$, $K_i \int_0^\tau e(\tau) d\tau$, and $K_d de(\tau)/dt$, respectively, which may be expressed in the ideal form of the equation $V_m(t) = K_p e(t) + K_i \int_0^\tau e(\tau) d\tau + K_d de(\tau)/dt$, where, $V_m(t)$ represents the computed modulating voltage 413 as a function of time in response to measured power at the output 404, the peak effective power calculation 410, and power set point 409.

Wherein:

$K_p e(t)$ represents the proportional reaction to error in the measured/calculated power to the desired power;

$K_i \int_0^\tau e(\tau) d\tau$ represents the integral reaction to the sum of the errors in the measured/calculated power to the desired power, where τ represents the period of time integrated over and e(t) represents the calculated power at the present time t; and, $K_d de(\tau)/dt$ represents the derivative reaction to the rate of change in the error of the measured/calculated power to the desired power.

In the most preferred embodiment, the PID equation may be expressed in the more common "standard" or "industrial" form $V_m(t) = K_p[e(t) + 1/T_i \int_0^\tau e(\tau) d\tau + T_d de(\tau)/dt]$, where, constants $K_i$ and $K_d$ are replaced with $T_i$ and $T_d$, representing the integral and derivative time values respectively. The standard form provides the advantage of simplifying the derivation and use of constants in the control equation.

In a preferred embodiment, time interval "t" of about 160 microseconds exists between power measurements and calculations of power at the target power output 404. The output calculation of the PID control loop of 411 may be referred to as the "manipulated variable" or modulating voltage 414 that is preferably used to drive amplifier block 403 to regulate output power closely about a set point. The constants $K_i$, $K_p$, and $K_d$ help to define how quickly circuit 400 may respond to increasing errors in output 404, or how quickly to modulate amplifier block 403 to reduce error in output at 404 as compared to set point 409. The power calculation 704 is preferably based on the quadrature 506 and in-phase 505 voltage components, and the quadrature 507 and in-phase 508 current components of the output of DDS block 401.

Figure 8:
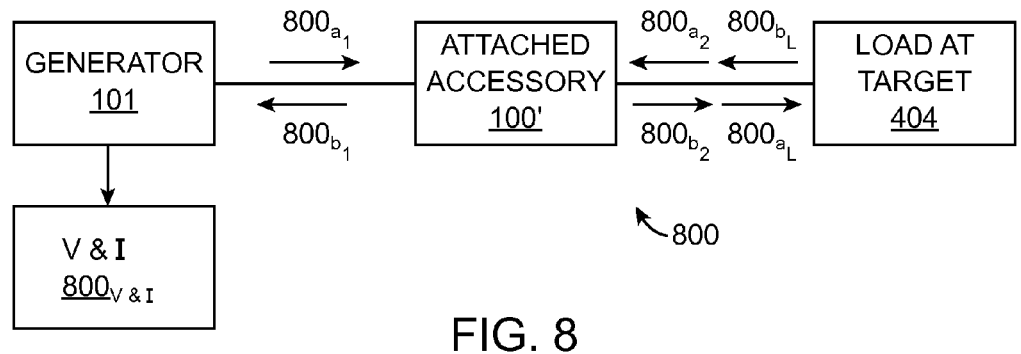
FIG. 8 schematically illustrates a two-port network design for sensing and controlling incident and reflected power.

Now referring to FIGS. 1 and 8, the overall apparatus 100, which includes both the power generator and control apparatus of enclosure 101 and an attached accessory 100' (which, for example, may comprise the catheter assembly 108 and connector 103 of FIG. 1), may utilize a communication schema such as that shown in FIG. 8. Although FIG. 8 depicts a preferred embodiment utilizing a two-port network 800, other numbers of communication ports may be employed depending on the desired arrangement for a given power control application. In general there are usually significant RF losses, reflections and phase shifts between voltage sensor 405, current sensor 407 and the target load (tissue) 404. These RF losses, reflections and phase shifts cause significant deviations in the actual power delivered to the load (tissue) 404 and additionally cause significant errors in the measurement of load (tissue) impedance. In a preferred embodiment, generalized 2-port reflectometry is used to compensate for all the RF losses, reflections and phase shifts in the RF path, both with respect to accurately controlling load (tissue) power and accurately measuring load (tissue) impedance. For this purpose, the two-port network 800 may comprise a series of control computations utilizing incident and reflected power waves between power generator and control apparatus of enclosure 101, attached accessory 100', and the load at the target power output 404, preferably resulting in controlled voltage and current output 800V&I by power generator and control apparatus of enclosure 101.

Incident power waves are denoted by subscript "$a_n$", reflected power waves are denoted by subscript "$b_n$", incident and reflected power at 404 are denoted by "$a_L$" and "$b_L$" respectively. For the purpose of clarity in the following description of the mathematic operations represented in FIG.

8, mathematic equations shall omit the descriptive element number "800" shown in FIG. 8 to simplify the meaning of the equations described.

The two-port network definition of scattering parameters in terms of incident and reflected power waves ($a_n$ and $b_n$, respectively) are defined as:

$$a_1 = \frac{1}{2}\left(\frac{V_1}{\sqrt{Z_o}} + I_1\sqrt{Z_o}\right). \qquad 1$$

$$b_1 = \frac{1}{2}\left(\frac{V_1}{\sqrt{Z_o}} - I_1\sqrt{Z_o}\right). \qquad 2$$

$$a_2 = \frac{1}{2}\left(\frac{V_2}{\sqrt{Z_o}} + I_2\sqrt{Z_o}\right). \qquad 3$$

$$b_2 = \frac{1}{2}\left(\frac{V_2}{\sqrt{Z_o}} - I_2\sqrt{Z_o}\right). \qquad 4$$

Wherein, a1 and b1 are the incident and reflected power waves at generator 101, and $a_2$ and $b_2$ are the incident and reflected power waves at the load (electrodes 112, for example).

The S-Parameter matrix for the two-port network along with expanded equations may be defined as:

$$\begin{pmatrix} b_1 \\ b_2 \end{pmatrix} = \begin{pmatrix} S_{11} & S_{12} \\ S_{21} & S_{22} \end{pmatrix} \begin{pmatrix} a_1 \\ a_2 \end{pmatrix}. \qquad 5$$

$$b_1 = S_{11}a_1 + S_{12}a_2. \qquad 6$$

$$b_2 = S_{12}a_1 + S_{22}a_2. \qquad 7$$

The complex impedances at the generator 101, which may comprise circuit 400, and at the load 404 may be respectively defined as rho ($\rho$) and gamma ($\Gamma$). Rho and gamma preferably may then be defined using the incident and reflected power waves as:

$$\rho = \frac{b_1}{a_1}. \qquad 8$$

$$\Gamma = \frac{a_2}{b_2}. \qquad 9$$

The reverse transform from rho space to gamma space may now be derived using the relationships in Equations 1 through 9, as shown below:

$$\frac{1}{\Gamma} = \frac{b_2}{a_2} = S_{22} + \frac{S_{12}a_1}{a_2}. \qquad 10$$

$$\frac{1}{\Gamma} - S_{22} = \frac{S_{12}a_1}{a_2}. \qquad 11$$

$$\frac{1}{\frac{1}{\Gamma} - S_{22}} = \frac{a_2}{S_{12}a_1}. \qquad 12$$

$$\frac{a_2}{a_1} = S_{12}\left(\frac{1}{\frac{1}{\Gamma} - S_{22}}\right). \qquad 13$$

-continued $$\rho = \frac{b_1}{a_1} = S_{11} + \frac{S_{12}a_2}{a_1}. \qquad 14$$

$$\rho = S_{11} + S_{12}^2\left(\frac{\Gamma}{1 - S_{22}\Gamma}\right). \qquad 15$$

$$\rho = S_{11} + S_{12}^2\left(\frac{\Gamma}{1 - S_{22}\Gamma}\right). \qquad 16$$

$$\rho = \frac{S_{11}(1 - S_{22}\Gamma) + S_{12}^2\Gamma}{1 - S_{22}\Gamma}. \qquad 17$$

$$\rho = \frac{S_{11} + (S_{12}^2 - S_{11}S_{22})\Gamma}{1 - S_{22}\Gamma}. \qquad 18$$

Equation 18 provides the explicit form of the reverse transform from rho space to gamma space. The scattering parameters may be grouped and preferably defined as reverse transform coefficients A, B, and D in the following form:

$$A = S_{11} \qquad 19.$$

$$B = S_{12}^2 - S_{11}S_{22} \qquad 20.$$

$$D = -S_{22} \qquad 21.$$

Equation 18 may be simplified by substituting coefficients A, B, and D into the preferred explicit form of the reverse transform, thereby providing a preferred general form of the reverse transform:

$$\rho = \frac{A + B\Gamma}{1 + D\Gamma}. \qquad 22$$

Using Equation 22, and solving for gamma, the forward transform may be derived in preferred form:

$$\rho + D\Gamma\rho = A + B\Gamma. \qquad 23$$

$$D\Gamma\rho - B\Gamma = A - \rho. \qquad 24$$

$$\Gamma(D\rho - B) = A - \rho. \qquad 25$$

$$\Gamma = \frac{A - \rho}{D\rho - B}. \qquad 26$$

$$\Gamma = \frac{\left(-\frac{A}{B}\right) + \frac{1}{B}\rho}{1 + \left(-\frac{D}{B}\right)\rho}. \qquad 27$$

In a similar fashion as Equations 19 through 21, forward transform coefficients A', B', and D' may preferably serve to simplify the equation between gamma and rho space as shown:

$$A' = \left(-\frac{A}{B}\right). \qquad 28$$

$$B' = \left(\frac{1}{B}\right). \qquad 29$$

$$D' = \left(-\frac{D}{B}\right). \qquad 30$$

Equation 12 may be simplified by substituting coefficients A', B', and D' into the preferred explicit form of the forward transform, thereby providing a preferred general form of the forward transform:

$$\Gamma = \frac{A' + B'\rho}{1 + D'\rho}. \qquad 31$$

Forward power at the load 404 may be preferably defined as the magnitude of the square of the power wave incident on load 404:

$$P_{FL} = |a_L|^2 = |b_2|^2 \qquad 32.$$

Similarly, the reverse power from load 404 may be defined as the magnitude of the square of the power wave reflected by load 404:

$$P_{RL} = |b_L|^2 = |a_2|^2 \qquad 33.$$

Through the relationships defined above, the power absorbed at the target power output load 404, may be defined as incident power minus reflected power through the relationships:

$$P_L = P_{AL} - P_{RL}. \qquad 34$$

$$P_L = |a_L|^2 - |b_L|^2. \qquad 35$$

$$P_L = |a_L|^2 \left\{ 1 - \frac{|b_L|^2}{|a_L|^2} \right\}. \qquad 36$$

and, substituting Equations 7, 9, and 32 into Equations 34 through 36, provides the expanded form of the relationships:

$$P_L = |a_L|^2 \{1 - |\Gamma|^2\} \qquad 37.$$

$$P_L = P_{FL} \{1 - |\Gamma|^2\} \qquad 38.$$

$$P_L = |b_2|^2 (1 - |\Gamma|^2) \qquad 39.$$

$$P_L = |S_{12}a_1 + S_{22}a_2|^2 (1 - |\Gamma|^2) \qquad 40.$$

In the most preferred two-port network, incident and reflected power at port 1 may now be defined. Incident power at 800$_{a1}$ may preferably be defined as the magnitude of the square of the power wave incident at 800$_{a1}$:

$$P_{F1} = |a_1|^2 \qquad 41.$$

and, reflected power at 800$_{b1}$ may preferably be defined as the magnitude of the square of the power wave reflected at 800$_{b1}$:

$$P_{R1} = |b_1|^2 \qquad 42.$$

Power absorbed at port 1 ("P$_1$") may be defined, using Equations 41 and 42, as the incident power at port 1 minus the reflected power at port 1:

$$P_1 = |a_1|^2 - |b_1|^2 = |a_1|^2 (1 - |\rho|^2) \qquad 43.$$

which, may also be defined as the magnitude of the absorbed voltage multiplied by the magnitude of the absorbed current multiplied by the cosine of the angle between the absorbed voltage and absorbed current:

$$P_1 = |V||I||\cos\phi| = |a_1|^2 (1 - |\rho|^2). \qquad 44$$

$$|a_1|^2 = \frac{|V||I||\cos\phi|}{(1 - |\rho|^2)}. \qquad 45$$

Substituting Equation 9 into Equation 7 and solving for $b_2$ may define the following relationships defined for 800$_{b2}$ in FIG. 8:

$$b_2 - S_{22}a_2 = S_{12}a_1. \qquad 46$$

$$b_2\left(1 - S_{22}\frac{a_2}{b_2}\right) = S_{12}a_1. \qquad 47$$

$$b_2(1 - S_{22}\Gamma) = S_{12}a_1. \qquad 48$$

$$b_2 = \frac{S_{12}a_1}{(1 - S_{22}\Gamma)}. \qquad 49$$

The power at load 404 in FIG. 8 may now be defined by substituting Equation 49 into Equation 39 and expanding the numerator by substituting Equation 45 into Equation 51:

$$P_L = \left|\frac{S_{12}a_1}{(1 - S_{22}\Gamma)}\right|^2 (1 - |\Gamma|^2). \qquad 50$$

$$P_L = \frac{|S_{12}|^2 |a_1|^2}{|(1 - S_{22}\Gamma)|^2} (1 - |\Gamma|^2). \qquad 51$$

$$P_L = \frac{|S_{12}|^2 |V||I||\cos\phi|(1 - |\Gamma|^2)}{(1 - |\rho|^2)|(1 - S_{22}\Gamma)|^2}. \qquad 52$$

Figure 16:
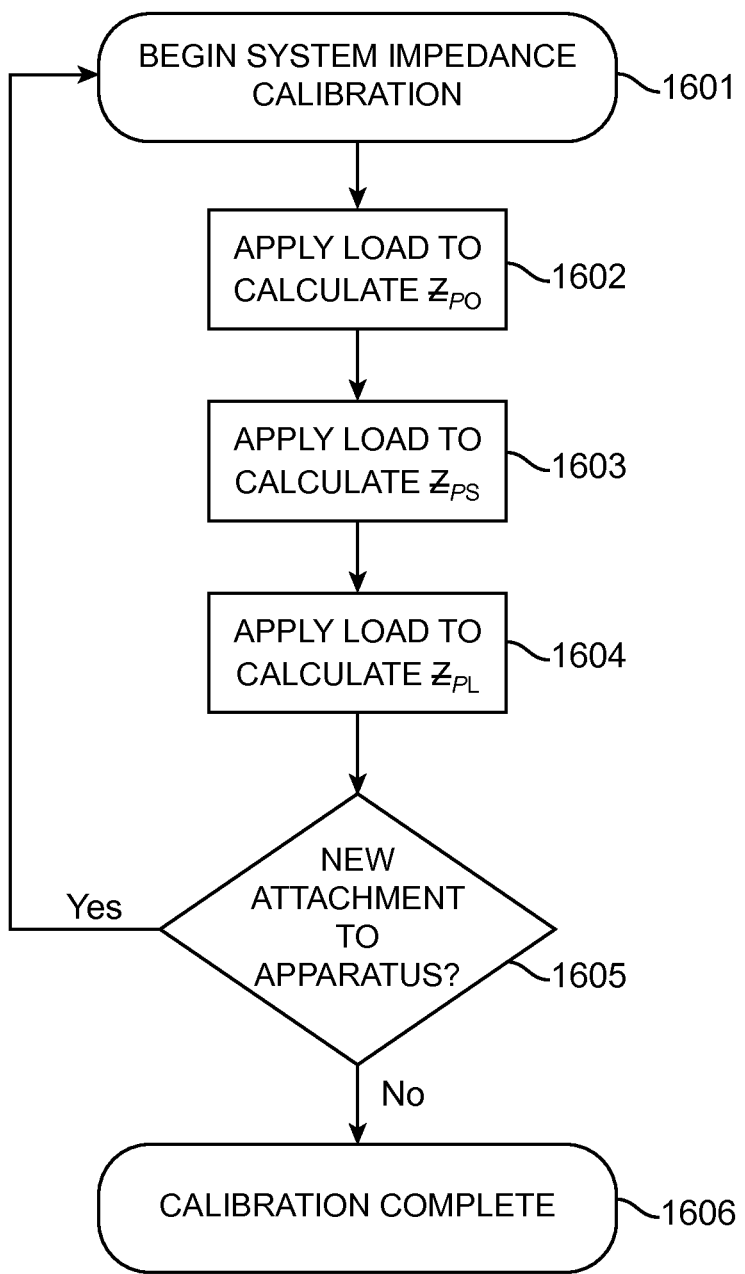
FIG. 16 schematically illustrates a method and system for calibrating a power generating system so as facilitate accurate measurement of impedance at a target power output.

In a preferred embodiment of the present invention, measurement of known impedances in circuit 400 of FIG. 4 may be made in order to define the transform coefficients A, B, D and A', B', D', as can be understood with reference to FIG. 16. Most preferably, three measurements are taken at known circuit loads 404, most preferably, impedance $Z_{\rho O}$ is taken at load of about 1000Ω, impedance $Z_{\rho S}$ is taken at a load of about 50Ω, and impedance $Z_{\rho L}$ is taken at a load of about 150Ω, where the complex voltage and current measurements (800$_{V\&I}$ of FIG. 8) at power generator and control apparatus 101 are used to calculate impedances $Z_{\rho O}$, $Z_{\rho S}$, and $Z_{\rho L}$ using Equation 53 where SYSTEM$_{IMPEDANANCE}$ is assigned the value 150Ω. However, known circuit loads and assigned SYSTEM$_{IMPEDANCE}$ to compute $Z_{\rho O}$, $Z_{\rho S}$, and $Z_{\rho L}$ may be performed at other values ranging between about zero Ohms and about infinite Ohms. As shown in FIG. 16, such a calibration method may begin 1601 prior to coupling of the power generation components to the target tissue, and ideally before coupling of attachment 100' to the power generation circuit 400 of enclosure 101. Three differing loads are applied with impedances being taken 1602, 1603, and 1604 at each load. These measurements are taken with the components of circuit 400, and are input into a hardware and/or software module for the system characterization calculations described herein.

$$Z_{\rho N} = \frac{\left(\frac{V_N}{I_N} - SYSTEM_{IMPEDANCE}\right)}{\left(\frac{V_N}{I_N} + SYSTEM_{IMPEDANCE}\right)}. \qquad 53$$

Solving Equation 53 may preferably involve a preliminary set of impedance measurements most preferably using network analysis, most preferably vector network analysis, to preferably provide impedances $Z_{\Gamma O}$, $Z_{\Gamma S}$, and $Z_{\Gamma L}$ at the respective loads of about 1000Ω, about 50Ω, and about 150Ω. The six preferred impedance measurements $Z_{\Gamma O}$, $Z_{\Gamma S}$, $Z_{\Gamma L}$ $Z_{\rho O}$, $Z_{\rho S}$, and $Z_{\rho L}$ may then preferably be used to calculate the transform coefficients A', B', D':

$$D' = \frac{(Z_{TS} - Z_{TO})*(Z_{\rho O} - Z_{\rho L}) - (Z_{TO} - Z_{TL})*(Z_{\rho S} - Z_{\rho O})}{(Z_{TO}*Z_{\rho O} - Z_{TS}*Z_{\rho S})*(Z_{\rho O} - Z_{\rho L}) - (Z_{TL}*Z_{\rho L} - Z_{TO}*Z_{\rho O})*(Z_{\rho S} - Z_{\rho O})}. \quad 54$$

$$B' = \frac{Z_{TO} - Z_{TL} - D*(Z_{TL}*Z_{\rho L} - Z_{TO}*Z_{\rho O})}{(Z_{\rho O} - Z_{\rho L})}. \quad 55$$

$$A' = Z_{TS} - B*Z_{\rho S} + D*(Z_{TS}*Z_{\rho S}). \quad 56$$

The value of the coefficients preferably defined by Equations 54 through 56 may now be preferably used to calculate actual load impedances at target power output 404 of FIG. 4 using Equation 31, and the actual power applied at target power output 404 using Equation 52, thereby preferably providing a calculated modulating output voltage 413 from PID controller 411 such that output at 404 is accurately regulated about a set point based on real-time changes in load, and power delivery is maintained within a range as described herein.

In preferred embodiments actual power output at the power delivery point is most preferably based on measured complex impedance angle of applied load at output 404. Wherein, the load most preferably denotes tissue and the complex impedance angle preferably denotes the health or disease of tissue and/or the change in tissue state through the course of the use of apparatus 100. Furthermore, because impedance is a function of capacitance and resistance, real-time tissue capacitance and real-time tissue resistance may also be known based on measured data through the relationship between impedance, capacitance, and resistance:

$$Z = (SYSTEM_{IMPEDANCE})*\frac{(1+\Gamma)}{(1-\Gamma)}. \quad 57$$

Recalling that impedance may have real and imaginary components, the relationship in Equation 57 may be further expressed and developed as follows:

$$Z = \frac{1}{\left(\frac{1}{R} + j\omega C\right)}. \quad 58$$

$$Z = \frac{1}{\left(\frac{1}{R} + j\omega C\right)}*\frac{(1-j\omega CR)}{(1-j\omega CR)}. \quad 59$$

$$Z = \frac{R - j\omega CR^2}{(1+\omega^2 C^2 R^2)}. \quad 60$$

$$Z_{real} = \frac{R}{(1+\omega^2 C^2 R^2)}. \quad 61$$

$$Z_{imaginary} = \frac{-j\omega CR^2}{(1+\omega^2 C^2 R^2)}. \quad 62$$

where $\omega$ denotes the natural frequency of the circuit, C denotes real-time tissue capacitance as measured at the load, and R denotes real-time tissue resistance as measured at the load.

Solving Equation 61 for $C^2$ and substituting Equation 63 into Equation 62, and solving Equation 64 for C:

$$C^2 = \frac{R - Z_{Real}}{(\omega^2 R^2 Z_{Real})}. \quad 63$$

$$Z_{Imaginary} = \frac{-j\omega CR^2}{\left(1 + \omega^2 R^2 * \frac{(R - Z_{Real})}{(\omega^2 R^2 Z_{Real})}\right)}. \quad 64$$

$$C = \frac{-Z_{Imaginary}}{Z_{Real}\omega R}. \quad 65$$

By solving Equation 65 for $\omega^2 C^2 R^2$ and substituting into Equation 61, the simplified relationship may be obtained:

$$Z_{real} = \frac{R}{\left(1 + \frac{Z_{Imaginary}}{Z_{Real}}\right)}. \quad 66$$

Now, the real-time tissue resistance may be determined through the known value of impedance Z from Equation 57 by simplifying Equation 66 and solving for R:

$$R = Z_{Real}*\left(1 + \left(\frac{Z_{Imaginary}}{Z_{Real}}\right)^2\right). \quad 67$$

and real-time tissue capacitance may be determined by substituting Equation 67 into Equation 65 and solving for C:

$$C = \frac{-Z_{Imaginary}}{Z_{Real}^2 \omega\left(1 + \left(\frac{Z_{Imaginary}}{Z_{Real}}\right)^2\right)}. \quad 68$$

In the most preferred embodiments of the system or overall apparatus 100 of FIG. 1 may include circuit 400 of FIG. 4 and coupling apparatus or accessory 100', which may together be employed in the characterization and selective treatment of tissue to promote a therapeutic response. The characterization and selective treatment of tissue based on impedance, imaging modalities, and energy modalities are described by U.S. Pat. No. 7,291,146 to Steinke, et al., issued on Nov. 6, 2007, entitled "Selectable Eccentric Remodeling and/or Ablation of Atherosclerotic Material", and the above referenced U.S. application Ser. Nos. 11/392,231, 11/975,651, 11/617,519, 11/975,474, 11/975,383, 12/564,268, the full disclosures of which are incorporated herein by reference. In the most preferred embodiments, power output is RF energy, however, ultrasound, laser, microwave, and the like as disclosed and described in the preceding references, are also within the scope of the present invention.

Now referring to FIG. 4, in some embodiments DDS block 401, power output set point control 409, and peak effective power sensor block 410 comprise a field programmable gate array without an embedded processor. In other embodiments where a field programmable gate array comprises an internal processor, DDS block 401, power output set point control 409, peak effective power sensor block 410, and PID controller may be comprised within the field programmable gate array.

In some embodiments, generator and control apparatus 101 may include a processor or be coupled to a processor to control or record treatment. The processor will typically comprise computer hardware and/or software, often including one or more programmable processor units running machine readable program instructions or code for implementing some, or all of, one or more of the embodiments and methods described herein. The code will often be embodied in a tangible media such as a memory (optionally a read only memory, a random access memory, a non-volatile memory, or the like) and/or a recording media (such as a floppy disk, a hard drive, a CD, a DVD, a non-volatile solid-state memory card, or the like). The code and/or associated data and signals may also be transmitted to or from the processor via a network connection (such as a wireless network, an ethernet, an internet, an intranet, or the like), and some or all of the code may also be transmitted between components of a catheter system and within the processor via one or more bus, and appropriate standard or proprietary communications cards, connectors, cables, and the like will often be included in the processor. The processor may often be configured to perform the calculations and signal transmission steps described herein at least in part by programming the processor with the software code, which may be written as a single program, a series of separate subroutines or related programs, or the like. The processor may comprise standard or proprietary digital and/or analog signal processing hardware, software, and/or firmware, and may preferably have sufficient processing power to perform the calculations described herein during treatment of the patient, the processor optionally comprising a personal computer, a notebook computer, a tablet computer, a proprietary processing unit, or a combination thereof. Standard or proprietary input devices (such as a mouse, keyboard, touchscreen, joystick, etc.) and output devices (such as a printer, speakers, display, etc.) associated with modern computer systems may also be included, and processors having a plurality of processing units (or even separate computers) may be employed in a wide range of centralized or distributed data processing architectures.

In the most preferred embodiments control software for apparatus 100 may use a client-server schema to further enhance system ease of use, flexibility, and reliability. "Clients" are the system control logic; "servers" are the control hardware. A communications manager delivers changes in system conditions to subscribing clients and servers. Clients "know" what the present system condition is, and what command or decision to perform based on a specific change in condition. Servers perform the system function based on client commands. Because the communications manager is a centralized information manager, new system hardware preferably may not require changes to prior existing client-server relationships; new system hardware and its related control logic may then merely become an additional "subscriber" to information managed through the communications manager. This control schema preferably provides the benefit of having a robust central operating program with base routines that are fixed; preferably no change to base routines may be necessary in order to operate new circuit components designed to operate with the system.

Accessories for Tissue Treatment

In some embodiments, the overall system or apparatus 100 of FIG. 1 may, along with the power generation apparatus, further include attached accessories, which most preferably may include an intraluminal catheter 108 having an energy delivery surface comprised therein.

In many embodiments, an energy delivery surface may preferably comprise a plurality of spaced electrodes 112. The power generating apparatus 101 as shown in FIG. 1 is operatively coupled to the plurality of electrodes by connector 103 so as to preferably allow the selective energizing of selected electrodes.

Figure 3A:
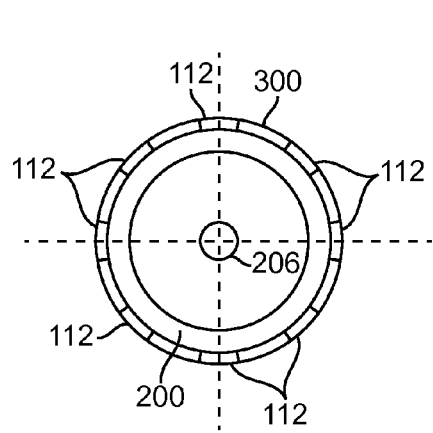
FIG. 3A schematically illustrates a cross-sectional view of the balloon of FIG. 2.

In many embodiments, the energy delivery surface comprises a plurality of electrodes 112 disposed about an expandable balloon 200, as shown in FIG. 3A, so as to define a plurality of remodeling zones in the target tissue when the balloon is expanded to come in contact with tissue such as that of a lumen.

Figure 2:
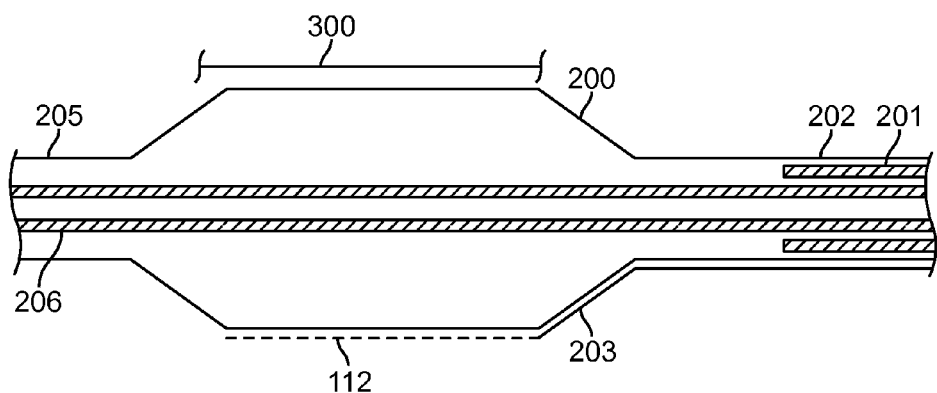
FIG. 2 schematically illustrates one embodiment of an inflatable balloon for use in the apparatus of FIG. 1.

Now referring to FIGS. 1 and 2, one exemplary embodiment of a catheter system inducing desirable temperature effects on tissue is shown. The catheter system includes a balloon catheter 108 having a catheter body 109 with a proximal end 107 and a distal end 111. Catheter body 109 is flexible and defines a catheter axis 113, and may include one or more lumens, such as a guidewire lumen 206 and an inflation lumen 201. Still further lumens may be provided if desired for other treatments or applications, such as perfusion, fluid delivery, imaging, or the like. Catheter 108 includes an inflatable balloon 200 adjacent distal end 111 and a housing 106 adjacent proximal end 107. Housing 106 includes a first connector 104 in communication with guidewire lumen 206 and a second connector 105 in fluid communication with inflation lumen 201. Inflation lumen 201 extends between balloon 200 and second connector 105. Both first and second connectors 104 and 105 may optionally comprise a standard connector, such as a LUER-LOC™ connector. A distal tip may include an integral tip valve to allow passage of guidewires, and the like.

Figure 3B:
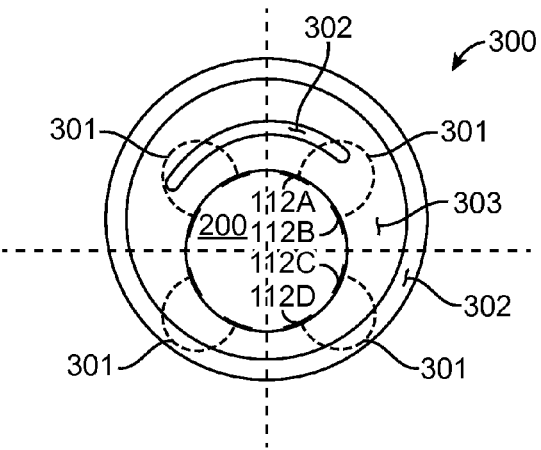
FIG. 3B schematically illustrates one embodiment of electrodes for use in tissue analysis and selective energy treatment using the apparatus of FIG. 1.

The housing 106 may also accommodate an electrical connector 103, which may preferably include a plurality of electrical connections, each electrically coupled to electrodes 112 via conductors 203. This arrangement preferably allows the electrodes 112 to be easily energized, the electrodes often being energized by an enclosed controller and power source 101, which may preferably produce energy in the form of monopolar or bipolar RF energy, microwave energy, ultrasound energy, or other such suitable forms of energy. In one such embodiment, the electrical connector 103 is coupled to circuit 400 of FIG. 4 that in its most preferable form may produce RF energy in a manner that may allow energy to be selectively directed to electrodes 112 as shown in FIG. 3B. When monopolar RF energy is employed, patient ground may, for example, be provided by an external electrode or an electrode on catheter body 109.

Now referring to FIGS. 3B and 1, the electrodes 112 are preferably coupled with the surrounding tissue 300, such that energy may be transmitted between the electrodes 112A, 112B, 112C, 112D and the tissue 300 so as to preferably initiate a biological response. The balloon 200 will typically comprise distal end 111 of a balloon catheter 108, and the energy delivery surfaces, such as electrodes 112, on the balloon 200 will generally be energized using an energy source coupled to proximal end 107 of catheter 108. An energy conduit 203 may extend along a catheter body 109 between the proximal end 107 and balloon 200, with the energy conduit 203 often comprising an electrical conductor for applying RF energy or the like, a light conductor such as a fiber optic filament running along a lumen in the catheter body so as to conduct laser or other light energies, or the like.

As shown in FIG. 3B, electrodes 112 may preferably be positioned circumferentially around balloon 200. Energy 301, most preferably RF energy, may in the most preferred embodiment be directed to adjacent pairs of electrodes 112A and 112C, or 112A and 112D, or any combination of electrodes 112A-112D, treating both the healthy portion of tissue 303 and diseased portion of tissue 302 within the surrounding tissue 300. This arrangement preferably creates an energy path 301 that may deliver energy or heat ("tissue remodeling energy") in particular treatment zones or segments to the tissue 300 between the electrode pairs 112A-112D ("remodeling zones") having a volume between the electrode pairs 112A-112D at a specific depth. Using different combinations of electrode pairs 112A-112D may reduce or eliminate gaps between the remodeling zones by using overlapping pairs. Using electrode pairs 112A-112D with bipolar energy preferably may thereby provide improved performance compared to a monopolar approach. Diseased tissue 302 is known to have higher electrical resistivity than healthy tissue 303. By using pairs of electrodes 112 in a bipolar system, such as 112A and 112B, tissue remodeling energy may preferably pass through healthy tissue 303, diseased tissue 302, or a combination thereof such that remodeling zones may be created. Any number of electrodes 112 may be used in different patterns or arrays to create any number of remodeling zones. Power generator and control apparatus 101 may apply constant power, constant voltage, constant current, or modulate to produce a constant temperature, whichever has the most advantage for the type of tissue and the desired therapeutic response.

Balloon 200 is illustrated in more detail in FIG. 2. Balloon 200 generally includes a proximal portion 202 coupled to inflation lumen 201 and a distal portion 205 coupled to guidewire lumen 206. Balloon 200 expands radially when inflated with a fluid or a gas. In some embodiments, balloon 200 may be a low-pressure balloon pressurized to contact the tissue 300. In other embodiments, balloon 200 may an angioplasty balloon capable of higher pressure to both heat the tissue 300 and expand the tissue 300 lumen. Balloon 200 may comprise a compliant or non-compliant balloon having folds to facilitate reconfiguring the balloon from a radially expanded, inflated configuration to a low profile configuration, particularly for removal after use.

Electrodes 112 are mounted on a surface of balloon 200, with associated conductors 203 extending proximally from the electrodes 112. Electrodes 112 may be arranged in many different patterns or arrays on balloon 200. The system may be used for monopolar or bipolar application of energy. For delivery of monopolar energy, a ground electrode may be used either on the catheter 108 shaft or on the patient's skin, such as a ground electrode pad. For delivery of bipolar energy, adjacent electrodes 112 may be axially offset to allow bipolar energy to be directed between adjacent circumferential (axially offset) electrodes 112. In other embodiments, electrodes 112 may be arranged in bands around balloon 200 to allow bipolar energy to be directed between adjacent distal and proximal electrodes 112.

Tissue Sensing and Selective Delivery of Therapeutic Energy Dosage

In many embodiments electrodes 112 may be energized to assess and then selectively treat targeted tissue 300, 302, 303 to preferably achieve a therapeutic result. For example, tissue signature may be used to identify tissue treatment regions with the use of impedance measurements. Impedance measurements utilizing circumferentially spaced electrodes 112 within a lumen, such as those shown in FIG. 3B, may be used to analyze tissue 300, 302, 303. Impedance measurements between pairs of adjacent electrodes 112 (and/or between pairs of separated electrodes 112A-112D) may differ when the current path passes through diseased tissue 302, and when it passes through healthy tissues 303 of a luminal wall for example. Hence, impedance measurements between the electrodes 112 on either side of diseased tissue 302 may indicate a lesion, while measurements between other pairs of adjacent electrodes 112 may indicate healthy tissue 303. Other characterization, such as intravascular ultrasound, optical coherence tomography, or the like may be used to identify regions to be treated either in conjunction with, or as an alternate to, impedance measurements. In some instances, it may be desirable to obtain baseline measurements of the tissues 300, 302, 303 to be treated preferably to help differentiate adjacent tissues, as the tissue signatures and/or signature profiles may differ from person to person. Additionally, the tissue signatures and/or signature profile curves may be normalized to facilitate identification of the relevant slopes, offsets, and the like between different tissues. Any of the techniques disclosed in U.S. Patent Application No. 60/852,787, filed on Oct. 18, 2006, entitled "Tuned RF Energy and Electrical Tissue Characterization For Selective Treatment Of Target Tissues", U.S. Provisional Application No. 60/921,973, filed on Apr. 4, 2007, entitled "Tuned RF Energy and Electrical Tissue Characterization For Selective Treatment Of Target Tissues", the full disclosures of which are incorporated herein by reference, may be combined with the present invention.

The power generator and control apparatus 101 may be employed to selectively energize the electrodes 112 in a range of power from about 0.001 Watts to about 50 Watts, a preferred exemplary range of about 0.25 to 5 Watts average power for about 1 to about 180 seconds, or with about 4 to about 45 Joules. Higher energy treatments are done at lower powers and longer durations, such as about 0.5 Watts for about 90 seconds or about 0.25 Watts for about 180 seconds. Most treatments in the 2 to 4 Watt range are performed in about 1 to about 4 seconds. If using a wider electrode 112 spacing, it would be preferable to scale up the average power and duration of the treatment, in which case the average power could be higher than about 5 Watts, and the total energy could exceed about 45 Joules. Likewise, if using a shorter or smaller electrode pair 112A-112D, it would be preferable to scale the average power down, and the total energy could be less than about 4 Joules. The power and duration are calibrated to be less than enough to cause severe damage, and most preferably, particularly less than enough to ablate diseased tissue within a blood vessel.

Suitable power ranges for providing the desired heating of the target tissue, and/or for limiting of heating to collateral tissues, may depend at least in part on the time for which energy is applied, on the electrode 112 (or other energy transmitting surface) geometry, and the like. First, when applying the treatments described herein to tissues with electrodes, there may be a preferred load impedance range for the tissues within the circuit so as to avoid having to apply voltages and/or currents that are outside desirable ranges, particularly when applying powers within ranges described herein. Suitable load impedance ranges would generally be within a range from about 20 Ohms to about 4500 Ohms, more typically being in a range from about 40 Ohms to about 2250 Ohms, and preferably being in a range from about 50 to about 1000 Ohms.

The load impedance of the tissue within the circuit may depend on the characteristics of the tissue, and also for example on the geometry of electrodes that engage the tissue, as the electrode geometries and polarity influence the geometry of the tissue effectively included within the circuit. The tissue to which energy is directed may have a specific conductivity in a range from about 0.2 Siemens per meter to about 0.5 Siemens per meter. Different types of diseased tissues may have specific conductivities in different ranges, with some types of diseased tissues having specific conductivities in a range from about 0.2 Siemens per meter to about 0.35 Siemens per meter, while others fall within a range from about 0.35 Siemens per to about 0.5 Siemens per meter.

Desired power, energy, and time of the treatment are likewise inter-related, and may also be at least related with electrode 112 geometry. Speaking very generally, lower power treatments applied for long times tends to result in treatments with relatively higher total energies, while higher power treatments for shorter times tends to result in lower energy treatments. More specifically, at relatively low average power (1 W or less) the total energy delivery per treatment may range from about 8 to about 45 Joules. At higher power (more than 1 W), the total energy delivery per treatment may range from about 4 to about 15 Joules. If the electrode spacing were doubled, power may increase by four times. The power transmitted into the tissue can be calibrated and scaled to the particular electrode configuration, often in order to keep the power and energy density in a desirable range. Exemplary power ranges may be, for example, from about 1 to about 5 Watts. The duration for the lower power settings typically varies from about 1 to about 8 seconds. Very low power settings of less than about 1 Watt are also possible, using durations much longer than about 10 seconds.

It is also possible to scale the power settings significantly by varying the electrode 112 configuration. If, for instance, the inner edge-to-edge spacing of the electrodes 112 is increased, roughly 4 times the power may be applied because the volume of tissue becomes roughly 4 times larger. As such, electrode configurations different from the exemplary embodiments described herein could be used within a power range of about 4 to about 20 Watts. Shortening the electrodes 112, and thus shortening and reducing the volume of the remodeling zones, would also affect the magnitude of the power that is appropriate to apply to the tissue volume.

In order to quantify this complex set of relationships, and bound the space within which the exemplary apparatus can operate, an empirical relationship between safe values of several of these parameters may be generated and provided graphically, in table form, or by a mathematical relationships. An exemplary equation describing a particularly advantageous relationship is:

$$\text{power} = bx^2 L t^{-0.59}$$

where b is a parameter in the range of 0.2 to 0.6, x is the inner edge-to-edge spacing of the electrodes 112 in millimeters, L is the length of the electrodes 112 in millimeters (and also the approximate length of the remodeling zone), the power is in Watts, and t is time in seconds. b has units of $(\text{Watts/mm}^3)*(\text{seconds}^{0.59})$. Exemplary treatments in the range described by this equation include treatments such as 4 Watts for 2 seconds, 3 Watts for 3 seconds, 2 Watts for 4 seconds, and 1 Watt for 12 seconds.

Calibration of circuit 400 may be performed by taking three measurements at known circuit loads 404, most preferably, impedance $Z_{\rho O}$ is taken at load of about 1000Ω, impedance $Z_{\rho S}$ is taken at a load of about 50Ω, and impedance $Z_{\rho L}$ is taken at a load of about 150Ω, where the complex voltage and current measurements ($800_{V\&I}$ of FIG. 8) at power generator and control apparatus 101 are used to calculate impedances $Z_{\rho O}$, $Z_{\rho S}$, and $Z_{\rho L}$. The preferred method of calibration may allow for accurate real-time measurement of impedance before and during treatment of tissue such that impedance may provide a means for tissue characterization and treatment control as disclosed and described herein.

Calibration of apparatus 100 may further comprise the step of identifying an accessory attached to the apparatus by repeating calibration to ascertain the type of attached accessory based on its impedance characteristics. For example, in FIG. 1 where the attached accessory comprises catheter 108 further comprised of electrodes 112, the number of electrodes 112 present may be determined by multiplexed sensing of the number of electrode circuits (such as electrodes 112 and conductors 203 as shown in FIG. 2) within the catheter 108 operably attached by connector 103 to power generator and control apparatus 102. Referring once again to FIGS. 1, 4, 8, and 16, after calibration of power generator circuit 400 without accessory 100' (typically catheter 108), the catheter can be attached to the power generator circuit 1603 and three impedance measurements can again be taken of the overall apparatus 100.

A number of advantages may be gained by preferably automatically reperforming calibration. For example, by having an entire apparatus assembly 100 calibrated, rather than a single subcomponent such as the various elements of circuit 400, the impedance measurements taken at load 404 may remain an accurate indicator for tissue characterization and power control irrespective of the attached accessory. Further, the sensed configuration of an attached accessory may correspond to a programmed treatment routine such that the dependencies of assorted configurations of electrodes 112 may correspond to the preferred duration and energy delivery parameters disclosed and described herein. Even further, preprogrammed recognition of attached accessories prevents the improper use of an accessory or the use of an incompatible attachment. Even further, the ability to detect the type of attached accessory may allow for a robust and simple accessory identification method that avoids complications associated with other identification methods such as radio frequency identification that may degrade during sterilization or interfere with the operation of other equipment. Moreover, a self-identification method may reduce or eliminate the need for user commands thereby improving ease of use and minimizing issues such as language barriers between user and apparatus. Additionally, the use of a graphical user interface 102 may be used as a further means to eliminate or reduce language dependencies and increase ease of use.

In many embodiments the power generation and control apparatus 101 may be programmed to operate within a range of impedance values measured at the power delivery target 404 such that above or below set limits the system may automatically shut down. For example, the apparatus 101 may be programmed to operate over a range of load impedance from about 5 Ohms to about 1000 Ohms, having a most preferred range of about 50 Ohms to about 500 Ohms, wherein the low end of the range may be suggestive of tissue that may be healthy or responsive to tissue, and the high end of the range may be suggestive of poor electrical contact or destruction of tissue. The programmed impedance limits may provide the advantage of a further safeguard in avoiding uncontrolled application of energy to locations in excess of desired dosage.

Figure 13:
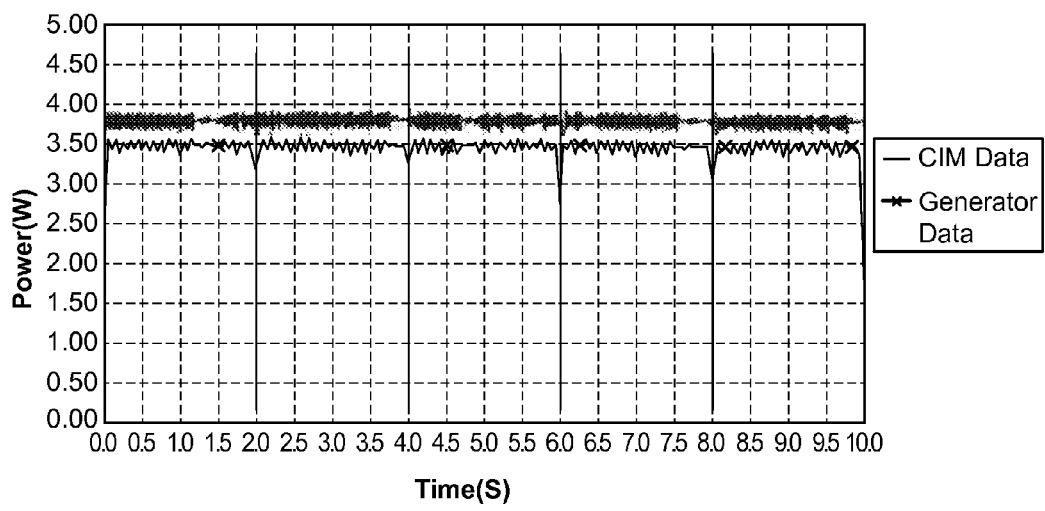
FIG. 13 is an exemplary plot of measured power at the target site and at the power generator in a tissue treatment embodiment of the apparatus shown in FIG. 1.

FIGS. 10-13 respectively show current, impedance, voltage, phase angle, and electrode power response in a typical tissue treatment employing gentle heating as controlled and delivered by the apparatus assembly of FIG. 1. In FIG. 13, the measured power at the target is shown in comparison to the power output at the generator.

Embodiments of the vascular treatment devices, systems, and methods described herein may be used to treat atherosclerotic disease by gentle heating in combination with gentle or standard dilation. For example, an angioplasty balloon catheter structure 108 having electrodes 112 disposed thereon might apply electrical potentials to the vessel wall before, during, and/or after dilation, optionally in combination with dilation pressures which are at or significantly lower than standard, unheated angioplasty dilation pressures. Where balloon 200 inflation pressures of about 10 to about 16 atmospheres may, for example, be appropriate for standard angioplasty dilation of a particular lesion, modified dilation treatments combined with appropriate electrical potentials, through flexible circuit electrodes 112, 203 on balloon 200, electrodes 112 deposited directly on the balloon structure 200, or the like, described herein may employ from about 10 to about 16 atmospheres or may be effected with pressures of about 6 atmospheres or less, and possibly as low as about 1 to about 2 atmospheres. Such moderate dilations pressures may, or may not, be combined with one or more aspects of the tissue characterization, tuned energy, eccentric treatments, and other treatment aspects described herein for treatment of diseases of the vasculature.

In many embodiments, gentle heating energy added before, during, and/or after dilation of a blood vessel may increase dilation effectiveness while lowering complications. In some embodiments, such controlled heating with balloon 200 may exhibit a reduction in recoil, providing at least some of the benefits of a stent-like expansion without the disadvantages of an implant. Benefits of the heating may be enhanced, and/or complications inhibited, by limiting heating of the vessel adventitial layer below a deleterious response threshold. In many cases, such heating of the vessel intima and/or media may be provided using heating times of less than about 10 seconds, often being less than about 3 (or even 2) seconds. In other cases, very low power may be used for longer durations. Efficient coupling of the energy 301 to the target tissue 300, 302, 303 by matching the driving potential of the circuit to the target tissue phase angle may enhance desirable heating efficiency, effectively maximizing the area under the electrical power curve. The matching of the phase angle need not be absolute, and while complete phase matching to a characterized target tissue may have benefits, alternative systems may pre-set appropriate potentials to substantially match typical target tissues; though the actual phase angles may not be matched precisely, heating localization within the target tissues may be significantly better than using a standard power form.

Remodeling may involve the application of energy, most preferably in the form of RF, but also microwave and/or ultrasound energy to electrodes 112, and the like. This energy will be controlled so as to limit a temperature of target and/or collateral tissues, for example, limiting the heating of a fibrous cap of a vulnerable plaque or the intimal layer of an artery structure.

In some embodiments, the surface tissue temperature range is from about 50° C. to about 90° C. For gentle heating, the tissue surface temperature may range from about 50° C. to about 65° C., while for more aggressive heating, the surface tissue temperature may range from about 65° C. to about 90° C. Limiting heating of a lipid-rich pool of a vulnerable plaque sufficiently to induce melting of the lipid pool while inhibiting heating of other tissues, such as an intimal layer or fibrous cap, to less than a tissue surface temperature in a range from about 50° C. to about 65° C., such that the bulk tissue temperature remains mostly below about 50° C. to about 55° C. may inhibit an immune response that might otherwise lead to restenosis, or the like. Relatively mild surface temperatures between about 50° C. and about 65° C. may be sufficient to denature and break protein bonds during treatment, immediately after treatment, and/or more than one hour, more than one day, more than one week, or even more than one month after the treatment through a healing response of the tissue to the treatment so as to provide a bigger vessel lumen and improved blood flow.

While the methods and devices described herein are not selective in tissue treatment of the blood vessels, the apparatus 100 can be used for treatment of both concentric and eccentric atherosclerosis, because atherosclerosis may be eccentric relative to an axis of the blood vessel over 50% of the time, and possibly in as much as (or even more than) 75% of cases.

Hence, remodeling of atherosclerotic materials may comprise shrinkage, melting, and the like, of atherosclerotic and other plaques. Atherosclerotic material within the layers of an artery may be denatured, melted and/or the treatment may involve a shrinking of atherosclerotic materials and/or delivery of bioactives within the artery layers so as to improve blood flow. The invention may also provide particular advantages for treatment of vulnerable plaques or blood vessels in which vulnerable plaque is a concern, which may comprise eccentric lesions. The invention will also find applications for mild heating of the cap structure to induce thickening of the cap and make the plaque less vulnerable to rupture, and/or heating of the lipid-rich pool of the vulnerable plaque so as to remodel, denature, melt, shrink, and/or redistribute the lipid-rich pool.

Controlled Application of Energy to Achieve Substantially Uniform Bulk Temperature Now referring to FIGS. 14A-15B, the controlled delivery of energy as a dosage may preferably be used to obtain a substantially uniform temperature distribution in bulk tissue by the selective distributed delivery of energy. Most preferably, tissue may be heated within a range of about 50° C. to about 70° C. to achieve a temperature preferably high enough to denature proteins and promote a healing response while avoiding tissue damage that may be caused at higher temperatures. Regulation of tissue temperature may be accomplished through direct temperature measurement using means such as a thermocouple, thermister, and the like. However, it may be advantageous to simplify the apparatus and to preferably avoid potential increases in device profile caused by the inclusion of wires or other sensing hardware into an intraluminal device. Because the present invention possesses the capability to deliver precise energy dosage and the capability to measure real-time changes in impedance at the point of power delivery, a uniform temperature distribution may be also achieved through these means.

In one preferred embodiment, tissue impedance may be used to infer tissue temperature conditions. The change in impedance as a function of time, or the derivative of the impedance slope (dz/dt), may be used to sense change in tissue temperature. Specifically, increase in impedance suggests tissue cooling given that tissue conductance is reduced as tissue cools. Conversely, decrease in impedance suggests tissue heating given that tissue conductance increases as tissue heats. Therefore, substantially constant tissue impedance, or dz/dt about equal to zero, may be used as a means to obtain a generally uniform temperature distribution through the sensing of impedance at the point of power delivery.

A distributed delivery of energy may be preferably employed to further aid in obtaining uniformity in bulk temperature. For example, electrodes 112A-L may be distributed about the circumference of a balloon. Electrodes 112A-L may be powered in a bipolar mode wherein alternate electrode pairs are powered such that in a first sequential application of energy every other electrode pair is powered at a discrete energy level for a discrete period of time. In a second sequential application of energy the electrode pairs not fired in the first sequential application of energy are powered. The configuration and ordering of power to electrode pairs to accomplish a particular temperature, for example 50° C., or 60° C., or 70° C., may be determined empirically. The duration of energy delivery in the form of sequential dosage to preferably maintain a substantially uniform temperature in the bulk tissue may then be controlled through tissue impedance measurement.

Although any variety of time for power, time between power, space between electrodes powered, and total energy delivered may be employed based on the specific nature of tissue to be heated, one preferred embodiment shown in FIG. 14A shows a substantially uniform temperature distribution by sequentially powering every other electrode pair for about 1.5 seconds at about 4 Watts, followed by sequentially powering the previously unpowered electrodes for about 1 second at about 4 Watts. The benefit of spaced sequential firing is that tissue may naturally heat, hold, and begin to cool such that high concentrations of heat are preferably avoided as compared to applying power without selective distribution. Once the initial power dosage is delivered, additional power may be applied as regulated trough tissue impedance measurement. In an alternate exemplary embodiment shown in FIG. 14B, power is delivered in the same sequential manner as described for FIG. 14A, however, the second sequential application of power follows a pause of about 30 seconds and the duration of the second sequential application of power may be increased to about 1.5 seconds.

In another exemplary embodiment, shown in FIGS. 15A-B, the use of accumulated damage theory, such as that described by the Arrhenius equation, may be employed to numerically predict energy dosage such that accumulated tissue temperature effects may be used to build a power dosage routine. A first sequential power delivery between every other electrode pair at about 4 Watts for about 5 seconds may be followed by a second sequential power delivery to the previously unpowered electrode pairs wherein the power level and time duration for each electrode pair in the second sequence may vary by position such that the accumulated heating and cooling of tissue preferably is accounted for such that a substantially uniform temperature distribution may be achieved. For example, the ordered second energizing sequence of electrode pairs may be about 4 Watts for about 0.45 seconds for the first electrode pair in the sequence, about 2.6 Watts for about 0.65 seconds for the second electrode pair in the sequence, about 1.8 Watts for about 1.15 seconds at the third pair, about 1.5 Watts for about 1.65 seconds at the fourth pair, about 1.3 Watts for about 3.15 seconds at the fifth pair, and about 1.1 Watts for about 5 seconds. In this example, the accumulated effect would preferably result in a tissue temperature of about 60° C. using a balloon with 12 electrodes distributed about the outer circumference of the balloon.

The use of accumulated damage theory may be tailored to specific types of tissue based on characterized tissue response curves such that power dosage routines may be developed specifically for accomplishing a certain temperature in a certain tissue type.

Additionally, whether using a damage accumulation model, or tissue impedance measurement to maintain bulk tissue temperature at a substantially uniform distribution, the energy dosage may vary, in part, based on electrode configuration as previously described herein.

Application of Energy to Modify Nerve Activity

In yet another exemplary embodiment of the present invention, the ability to deliver energy in a targeted dosage may be used for nerve tissue in order to achieve beneficial biologic responses. For example, chronic pain, urologic dysfunction, hypertension, and a wide variety of other persistent conditions are known to be affected through the operation of nervous tissue. For example, it is known that chronic hypertension that may not be responsive to medication may be improved or eliminated by disabling excessive nerve activity proximate to the renal arteries. It is also known that nervous tissue does not naturally possess regenerative characteristics. Therefore it may be possible to beneficially affect excessive nerve activity by disrupting the conductive pathway of the nervous tissue. When disrupting nerve conductive pathways, it is particularly advantageous to avoid damage to neighboring nerves or organ tissue. The ability to direct and control energy dosage is well-suited to the treatment of nerve tissue. Whether in a heating or ablating energy dosage, the precise control of energy delivery as described and disclosed herein may be directed to the nerve tissue. Moreover, directed application of energy may suffice to target a nerve without the need be in exact contact as would be required when using a typical ablation probe. For example, eccentric heating may be applied at a temperature high enough to denature nerve tissue without causing ablation and without requiring the piercing of luminal tissue. However, it may also be preferable to configure the energy delivery surface of the present invention to pierce tissue and deliver ablating energy similar to an ablation probe with the exact energy dosage being controlled by the power control and generation apparatus 101.

Referring again to the example of renal hypertension involving the reduction of excessive nerve activity, FIG. 3B may be used to describe a non-piercing, non-ablating way to direct energy to affect nerve activity. Nerve tissue may be located in some location in tissue 300, 302, 303 surrounding the lumen of the renal artery. Electrodes 112 on balloon 200 may be powered to deliver energy 301 in the known direction of a nerve to be affected, the depth of energy penetration being a function of energy dosage. Moreover, empirical analysis may be used to determine the impedance characteristics of nervous tissue such that apparatus 101 may be used to first characterize and then treat tissue in a targeted manner as disclosed and described herein. The delivery and regulation of energy may further involve accumulated damage modeling as well.

While the exemplary embodiments have been described in some detail, by way of example and for clarity of understanding, those of skill in the art will recognize that a variety of modification, adaptations, and changes may be employed.

What is claimed is:

1. A power generating apparatus for treatment of tissue having a circuit comprising:
   a direct digital synthesizer (DDS) operatively coupled to a power amplifier;
   a power output set point controller providing a signal;
   a peak effective power sensor receiving voltage and current feedback measured during delivery of power from the circuit to a power delivery target, the peak effective power sensor providing a signal based on the feedback; and
   a PID controller, operatively coupled to receive the signals from the power output set point controller and the peak effective power sensor, and operatively coupled to direct a modulating voltage signal to the power amplifier such that output of power from the circuit is maintained within a range about a power output set point in response to the signal from the peak effective power sensor, wherein the output of power from the circuit is continuously maintained during a treatment period,
   wherein the power amplifier is comprised of a variable gain amplifier and a linear power amplifier operatively coupled in series.

2. The power generating apparatus of claim 1 wherein a digital-to-analog converter is coupled between the DDS and power amplifier.

3. The power generating apparatus of claim 1 wherein energy output is RF energy.

4. The power generating apparatus of claim 1 wherein the power delivery target is comprised of tissue.

5. The power generating apparatus of claim 1 wherein the DDS, power output set point controller, and peak effective power sensor comprise a field programmable gate array.

6. The power generating apparatus of claim 1 wherein the power amplifier is comprised of a linear power amplifier whose maximum output voltage is controlled by the current flowing in the power amplifier.

7. The power generating apparatus of claim 6 wherein output voltage from the linear power amplifier to the power delivery target during use comprises RF output voltage having a maximum available output limit over a range of load impedances of about 50 Ohm to about 500 Ohms.

8. The power generating apparatus of claim 6 wherein the maximum output voltage from the linear power amplifier limits the power dissipation within the power amplifier.

9. The power generating apparatus of claim 6 wherein the linear power amplifier controls the maximum output voltage using switched mode technology.

10. The power generating apparatus of claim 1 wherein the modulating voltage signal from the PID controller is received by the variable gain amplifier.

11. The power generating apparatus of claim 1 wherein the peak effective power sensor comprises a DDS, a current circuit further comprising square root and inverse tangent gates in parallel, and a voltage circuit further comprising square root and inverse tangent gates in parallel.

12. The power generating apparatus of claim 11 wherein the DDS of the peak effective power sensor has a voltage output with a low-pass filter, and a current output with a low-pass filter.

13. The power generating apparatus of claim 11 wherein output of the inverse tangent gates for the current circuit and the voltage circuit are operatively coupled to pass through a cosine gate.

14. The power generating apparatus of claim 1 wherein the voltage and current feedback from the power delivery target to the peak effective power sensor each comprise in-phase and quadrature signal components.

15. The power generating apparatus of claim 1 wherein the signal from the peak effective power sensor represents the effective power output of the circuit at the power delivery target.

16. The power generating apparatus of claim 1 wherein the power output set point is about 0.001 Watts to about 50 Watts.

17. The power generating apparatus of claim 1 wherein the power output modulates about the set point by a maximum of about ±20%.

18. The power generating apparatus of claim 1 wherein the power output modulates about the set point by a maximum of about ±10%.

19. The power generating apparatus of claim 1 wherein the power output modulates about the set point by a maximum of about ±5%.

20. The power generating apparatus of claim 1 wherein the power output modulates about the set point by a maximum of about ±2%.

21. A power generating apparatus for treatment of tissue comprising:
a DDS operatively coupled to a RF power amplifier;
a RF power output set point controller providing a signal;
a peak effective RF power sensor receiving voltage and current feedback measured at a RF power delivery target during RF power delivery to the power delivery target, the peak effective RF power sensor providing a signal based on the feedback; and
a controller, operatively coupled to receive the signals from the RF power output set point controller and the peak effective RF power sensor, and operatively coupled to direct a modulating voltage signal to the RF power amplifier such that the output of RF power from the circuit is maintained within a range about the RF power output set point in response to the signal provided by the peak effective RF power sensor, wherein the output of RF power from the circuit is continuously maintained during a treatment period,
wherein the power amplifier is comprised of a variable gain amplifier and a linear power amplifier operatively coupled in series.

22. A power generating and control apparatus for eccentric remodeling treatment of tissue about a lumen, the apparatus comprising:
a DDS operatively coupled to a RF power amplifier;
a RF power output set point controller providing a signal;
a peak effective RF power sensor receiving voltage and current feedback measured at the tissue during RF power delivery about the circumference of the lumen, the peak effective RF power sensor providing a signal based on the feedback; and
a controller, operatively coupled to receive the signals from the RF power output set point controller and the peak effective RF power sensor, and operatively coupled to direct a modulating voltage signal to the RF power amplifier such that the output of RF power from the circuit is maintained within a therapeutic tissue remodeling range about the RF power output set point in response to the signal provided by the peak effective RF power sensor, wherein the output of RF power from the circuit is continuously maintained during a treatment period,
wherein the power amplifier is comprised of a variable gain amplifier and a linear power amplifier operatively coupled in series.

23. A power generating apparatus for treatment of a target tissue, the power generating apparatus comprising:
a frequency synthesizer generating a frequency signal;
a power amplifier operatively coupling the frequency synthesizer to a power output, the output coupleable to the target tissue;
a power sensor configured to receive voltage and current feedback from the target tissue during power output delivery to the target tissue and to output a signal based on the voltage and current feedback; and
a controller coupling the power sensor to the power amplifier, the controller having an input for receiving a power set point and transmitting, in response to the power set point and the signal from the power sensor, a modulating signal to the power amplifier such that power output from the power amplifier to the target tissue per the frequency signal is maintained within a range about the power set point, wherein the output of power from the power amplifier is continuously maintained during a treatment period,
wherein the power amplifier is comprised of a variable gain amplifier and a linear power amplifier operatively coupled in series.

24. The power generating apparatus of claim 23 wherein the frequency synthesizer comprises a digital frequency synthesizer, and wherein a digital-to-analog converter couples the frequency synthesizer to the power amplifier.

25. The power generating apparatus of claim 23 wherein energy output to the target comprises RF energy.

* * * * *